US006451564B1

(12) United States Patent
Guillouet et al.

(10) Patent No.: US 6,451,564 B1
(45) Date of Patent: Sep. 17, 2002

(54) METHODS FOR PRODUCING L-ISOLEUCINE

(75) Inventors: Stephane Guillouet, Toulouse Cedex (FR); Avital A. Rodal, Waltham, MA (US); Philip A. Lessard, Framingham, MA (US); Anthony J. Sinskey, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/608,065

(22) Filed: Jun. 30, 2000

Related U.S. Application Data
(60) Provisional application No. 60/142,071, filed on Jul. 2, 1999, and provisional application No. 60/205,212, filed on May 18, 2000.

(51) Int. Cl.[7] ............................. C12P 13/06; C12N 1/21
(52) U.S. Cl. ............... 435/116; 435/252.32; 435/254.1; 435/254.11; 435/419; 800/295
(58) Field of Search ..................... 435/116, 252.3, 435/252.32, 254.11, 419, 113, 115, 109, 455, 254.1; 800/295

(56) References Cited

U.S. PATENT DOCUMENTS

| | | | |
|---|---|---|---|
| 4,649,119 A | 3/1987 | Sinskey et al. | 435/320.1 |
| 4,769,061 A | 9/1988 | Comai | 504/206 |
| 4,940,835 A | 7/1990 | Shah et al. | 800/288 |
| 4,965,197 A | 10/1990 | Liebl et al. | 435/69.8 |
| 4,975,374 A | 12/1990 | Goodman et al. | 435/183 |
| 4,980,285 A | 12/1990 | Sano et al. | 435/108 |
| 5,135,859 A | 8/1992 | Witholt et al. | 435/135 |
| 5,185,262 A | 2/1993 | Kohama et al. | 435/320.1 |
| 5,229,279 A | 7/1993 | Peoples et al. | 435/135 |
| 5,245,023 A | 9/1993 | Peoples et al. | 536/23.2 |
| 5,250,430 A | 10/1993 | Peoples et al. | 435/232 |
| 5,334,520 A | 8/1994 | Dennis | 435/135 |
| 5,344,769 A | 9/1994 | Witholt et al. | 435/135 |
| 5,426,050 A | 6/1995 | Morinaga et al. | 435/252.32 |
| 5,480,794 A | 1/1996 | Peoples et al. | 435/232 |
| 5,518,907 A | 5/1996 | Dennis | 435/141 |
| 5,534,432 A | 7/1996 | Peoples et al. | 800/298 |
| 5,602,321 A | 2/1997 | John | 800/314 |
| 5,610,041 A | 3/1997 | Somerville et al. | 800/264 |
| 5,631,150 A | 5/1997 | Harkki et al. | 435/105 |
| 5,641,660 A | 6/1997 | Sinskey et al. | 435/115 |
| 5,650,555 A | 7/1997 | Somerville et al. | 800/264 |
| 5,661,026 A | 8/1997 | Peoples et al. | 435/252.3 |
| 5,663,063 A | 9/1997 | Peoples et al. | 435/135 |
| 5,707,828 A | 1/1998 | Sreekrishna et al. | 435/69.1 |
| 5,759,828 A | 6/1998 | Tal et al. | 435/69.1 |
| 5,766,925 A | 6/1998 | Sugimoto et al. | 435/252.32 |
| 5,792,933 A | 8/1998 | Ma | 800/287 |
| 5,811,272 A | 9/1998 | Snell et al. | 435/135 |
| 5,882,883 A | 3/1999 | Egel-Mitani et al. | 435/43 |
| 5,888,783 A | 3/1999 | Tomita et al. | 435/115 |
| 5,891,686 A | 4/1999 | Dennis et al. | 435/135 |
| 5,919,670 A | 7/1999 | Okamoto et al. | 435/106 |
| 5,940,660 A | 8/1999 | Gruys et al. | 800/298 |
| 5,942,662 A | 8/1999 | Ryals et al. | 800/300 |
| 5,948,612 A | 9/1999 | Bascomb et al. | 435/6 |
| 5,952,553 A | 9/1999 | Croughan | 800/320.2 |
| 5,958,745 A | 9/1999 | Gruys et al. | 435/183 |
| 5,959,179 A | 9/1999 | Hinchee et al. | 800/298 |
| 5,990,390 A | 11/1999 | Lundquist et al. | 800/302 |
| 5,994,622 A | 11/1999 | Jofuku et al. | 800/260 |
| 6,005,168 A | 12/1999 | Steiger et al. | 800/312 |
| 6,022,729 A | 2/2000 | Steinbüchel et al. | 435/252.3 |
| 6,071,998 A | 6/2000 | Muller et al. | 524/494 |
| 6,083,729 A | 7/2000 | Martin et al. | 435/135 |
| 6,091,002 A | 7/2000 | Asrar et al. | 800/288 |
| 6,117,658 A | 9/2000 | Dennis et al. | 435/135 |
| 6,175,061 B1 | 1/2001 | Bright et al. | 800/298 |

FOREIGN PATENT DOCUMENTS

| | | |
|---|---|---|
| EP | 0 333 033 A1 | 9/1989 |
| EP | 0 242 246 B1 | 11/1992 |
| EP | 0685555 A1 * | 5/1995 |
| WO | WO 88/09819 | 12/1988 |
| WO | WO 92/12250 | 7/1992 |
| WO | WO 99/02656 | 1/1999 |
| WO | WO 99/41395 | 8/1999 |

OTHER PUBLICATIONS

S. Morbach et al. Engineering the homoserine dehydrogenase and threonine dehydratase control points to analyse flux towards L–isoleucine in *Corynebacterium glutamicum* Appl Microbiol Biotechnol 1996, 45:612–620.*

An, G.–H. et al., "Redirection of Carbon Flux to Lysine in a Recombinant of *Corynebacterium lactofermentum* ATCC 21799 by Limited Supply of Pantothenate," *J. Biosci. Bioengineering* 88:168–172, The Society for Bioscience and Bioengineering, Elsevier Science (Aug. 1999).

(List continued on next page.)

*Primary Examiner*—Remy Yucel
*Assistant Examiner*—Bronwen M. Loeb
(74) *Attorney, Agent, or Firm*—Sterne, Kessler, Goldstein and Fox P.L.L.C.

(57) ABSTRACT

The present invention relates, in general, to the overproduction of L-isoleucine by nonhuman organisms. More specifically, the present invention relates to methods for producing L-isoleucine comprising: (a) growing a transformed nonhuman organism under conditions that provide for synthesis of L-isoleucine, wherein the nonhuman organism comprises one or more copies of a transgene comprising at least one nucleotide sequence encoding catabolic threonine dehydratase; wherein the L-isoleucine is synthesized by the transformed nonhuman organism, the synthesis being greater than that of the corresponding non-transformed nonhuman organism; and (b) recovering the L-isoleucine from the culture medium in which the transformed nonhuman organism was cultured.

41 Claims, 8 Drawing Sheets

OTHER PUBLICATIONS

Archer, J.A.C. et al., "A C–terminal deletion in *Corynebacterium glutamicum* homoserine dehydrogenase abolishes allosteric inhibition by L–threonine," *Gene* 107:53–59, Elsevier Science Publishers, B.V. (1991).

Archer, J.A.C. and A.J. Sinskey, "The DNA sequence and minimal replicon of the *Corynebacterium glutamicum* plasmid pSR1: evidence of a common ancestry with plasmids from *C. diptheriae*," *J. Gen. Microbiol.* 139:1753–1759, Society for General Microbiology (1993).

Benner, S.A., "Enzyme Kinetics and Molecular Evolution," *Chem. Rev.* 89:789–806, American Chemical Society (1989).

Bevan, M.W. and M.–D. Chilton, "T–DNA of the Agrobacterium Ti and Ri Plasmids," *Ann. Rev. Genet.* 16:357–384, Annual Reviews Inc. (1982).

Bhadra, R. and P. Datta, "Allosteric Inhibition and Catabolite Inactivation of Purified Biodegradative Threonine Dehydratase of *Salmonella typhimurium*," *Biochem.* 17:1691–1699, American Chemical Society (1978).

Binding, H., "Regeneration of Plants", in *Plant Protoplasts*, Fowke and Constabel, eds., CRC Press, Inc., Boca Raton, pp. 21–37, CRC Press, Inc. (1985).

Bradford, M.M., "A Rapid and Sensitive Method for the Quantitation of Microgram Quantities of Protein Utilizing the Principle of Protein–Dye Binding," *Anal. Biochem.* 72:248–254, Academic Press, Inc. (1976).

Colon, G. et al., "Redirection of Carbon Flux at a *Corynebacterium glutamicum* Threonine Metabolic Branchpoint by Controlled Enzyme Over–Expression," *Abst. General Meeting Amer. Soc. Microbiol.* 93:320, Abstract No. 0–11, American Society for Microbiology (1993).

Colón, G.E. et al., "Effect of Inducible thrB Expression on Amino Acid Production in *Corynebacterium lactofermentum* ATCC 21799," *Appl. Environ. Microbiol.* 61:74–78, American Society for Microbiology (1995).

Colón, G.E. et al., "Production of isoleucine by overexpression of ilvA in a *Corynebacterium lactofermentum* threonine producer," *Appl. Microbiol. Biotechnol.* 43:482–488, Springer–Verlag (1995).

De Greef, W. et al., "Evaluation of Herbicide Resistance in Transgenic Crops Under Field Conditions," *Bio/Technology* 7: 61–64, Nature Publishing Company (1989).

DeBlock, M. et al., "Engineering herbicide resistance in plants by expression of a detoxifying enzyme," *EMBO J.* 6: 2513–2518, IRL Press Ltd. (1987).

Duncan, B.K. and B. Weiss, "Specific Mutator Effects of ung (Uracil–DNA Glycosylase) Mutations in *Escherichia coli*," *J. Bacteriol.* 151:750–755, American Society for Microbiology (1982).

Eggeling, I. et al., "Regulation of acetohydroxy acid synthase in *Corynebacterium glutamicum* during fermentation of α–ketobutyrate to L–isoleucine," *Appl. Microbiol. Biotechnol.* 25:346–351, Springer–Verlag (1987).

Eggeling, L. et al., "Improved L–lysine yield with *Corynebacterium glutamicum*: use of dapA resulting in increased flux combined with growth limitation," *Appl. Microbiol. Biotechnol.* 49:24–30, Springer–Verlag (Jan. 1998).

Evans, D.A. and J.E. Bravo, "Protoplast Isolation and Culture," in *Handbook of Plant Cell Culture, vol. 1. Techniques for Propagation and Breeding*, Evans, D.A. et al., eds., MacMillan Publishing Company, New York, pp. 124–176, Macmillan Publishing Co. (1983).

Feldman, D.A. and P. Datta, "Catabolite Inactivation of Biodegradative Threonine Dehydratase of *Escherichia coli*," *Biochem.* 14:1760–1767, American Chemical Society (1975).

Follettie, M.T. and A.J. Sinskey, "Recombinant DNA Technology for *Corynebacterium Glutamicum*," *Food Technol.* 40:88–94, Institute of Food Technologists (1986).

Follettie, M.T. et al., "Organization and regulation of the *Corynebacterium glutamicum* hom–thrB and thrC loci," *Mol. Microbiol.* 2:53–62, Blackwell Scientific Publications (1988).

Follettie, M.T. et al., "Gene Structure and Expression of the *Corynebacterium flavum* N13 ask–asd Operon," *J. Bacteriol.* 175:4096–4103, American Society for Microbiology (1993).

Goss, T.J. and P.Datta, "Molecular cloning and expression of the biodegradative threonine dehydratase gene (tdc) of *Escherichia coli* K12," *Mol. Gen. Genet.* 201:308–314, Springer–Verlag (1985).

Gubler, M. et al., "Cloning of the Pyruvate Kinase Gene (pyk) of *Corynebacterium glutamicum* and Site–Specific Inactivation of pyk in a Lysine–Producing *Corynebacterium lactofermentum* Strain," *Appl. Environ. Microbiol.* 60:2494–2500, American Society for Microbiology (1994).

Guillouet, S. et al., "Expression of the *Escherichia coli* Catabolic Threonine Dehydratase in *Corynebacterium glutamicum* and Its Effect on Isoleucine Production," *Appl. Environ. Microbiol.* 65:3100–3107, American Society for Microbiology (Jul. 1999).

Han, K.–S. et al., "The molecular structure of the *Corynebacterium glutamicum* threonine synthase gene," *Molec. Microbiol.* 4:1693–1702, Blackwell Scientific Publications in association with the Incorporating Microbiological Sciences (IUMS) (1990).

Hashiguchi, K.–i. et al., "Effects of an *Escherichia coli* ilvA Mutant Gene Encoding Feedback–resistant Threonine Deaminase on L–Isoleucine Production by *Brevibacterium flavum*," *Biosci. Biotech. Biochem.* 61:105–108, Japan Society for Bioscience, Biotechnology, and Agrochemistry (1997).

Horton, R.M. et al.,. "Engineering hybrid genes without the use of restriction enzymes: gene splicing by overlap extension," *Gene* 77: 61–68, Elsevier Scientific Publishers B.V. (1989).

Jetten, M.S.M. et al., "Molecular Organization and Regulation of the Biosynthetic Pathway for Aspartate–Derived Amino Acids in *Corynebacterium glutamicum*," in *Industrial Microorganisms: Basic and Applied Molecular Genetics*, Baltz, R.H., et al., eds., Am. Soc. Microbiol., Washington, DC, pp. 97–104 (1993).

Jetten, M.S.M. et al., "Regulation of phospho(enol)–pyruvate– and oxaloacetate–converting enzymes in *Corynebacterium glutamicum*," *Appl. Microbiol. Biotechnol.* 41:47–52, Springer–Verlag (1994).

Jetten, M.S.M. et al., "Structural and Functional Analysis of Pyruvate Kinase from *Corynebacterium glutamicum*," *Appl. Environ. Microbiol.* 60:2501–2507, American Society for Microbiology (1994).

Jetten, M.S.M. et al., "Effect of different levels of aspartokinase on the lysine production by *Corynebacterium lactofermentum*," *Appl. Microbiol. Biotechnol.* 43:76–82, Springer–Verlag (1995).

Kelle, R. et al., "Glucose–controlled L–isoleucine fed–batch production with recombinant strains of *Corynebacterium glutamicum*," *J. Biotechnol. 50*:123–136, Elsevier Science B.V. (1996).

Klee, H. et al., "Agrobacterium–Mediated Plant Transformation and Its Further Applications to Plant Biology," *Ann. Rev. Plant Physiol. 38:* 467–486, Annual Reviews Inc. (1987).

Klein, T. M. et al., "High–velocity microprojectiles for delivering nucleic acids into living cells," *Nature 327:* 70–73, Macmillan Publishers Ltd. (1987).

Koziel, M.G. et al., "Field Performance of Elite Transgenic Maize Plants Expressing an Insecticidal Protein Derived from *Bacillus thuringiensis,*" *Biotechnology 11:* 194–200, Nature Publishing Co. (1993).

Lee, K.Y. et al., "The molecular basis of sulfonylurea herbicide resistance in tobacco," *EMBO J. 7:* 1241–1248, IRL Press Ltd. (1988).

Lessard, P.A. et al., "Corynebacteria, Brevibacteria," in *Encyclopedia of Bioprocess Technology: Fermentation, Biocatalysis and Bioseparation,* vol. 2, Flickinger et al, eds, John Wiley & Sons, Inc., New York, NY, pp. 729–740 (Apr. 1999).

Marshall, L.C. et al., "Allelic mutations in acetyl–coenzyme A carboxylase confer herbicide tolerance in maize," *Theor. Appl. Genet. 83:* 435–442, Springer–Verlag (1992).

Miki, B.L. et al., "Transformation of *Brassica napus* canola cultivars with *Arabidopsis thaliana* acetohydroxyacid synthase genes and analysis of herbicide resistance," *Theor. Appl. Genet. 80:* 449–458, Springer–Verlag (1990).

Möckel, B. et al., "Threonine dehydratases of *Corynebacterium glutamicum* with altered allosteric control: their generation and biochemical and structural analysis," *Mol. Microbiol. 13*:833–842, Blackwell Scientific Publications (1994).

Morbach S. et al., "Use of Feedback–Resistant Threonine and Dehydratases of *Corynebacterium glutamicum* To Increase Carbon Flux towards L–Isoleucine," *Appl. Environ. Microbiol. 61*:4315–4320, American Society for Microbiology (1995).

Paszkowski, J. et al., "Direct gene transfer to plants," *EMBO J. 3:* 2717–2722, IRL Press Ltd. (1984).

Pátek, M. et al., "Leucine Synthesis in *Corynebacterium glutamicum:* Enzyme Activities, Structure of leuA, and Effect of leuA Inactivation on Lysine Synthesis," *Appl. Environ. Microbiol. 60*:133–140, American Society for Microbiology (1994).

Pittard, J. and E.A. Adelberg, "Gene Transfer by F' Strains of *Escherichia Coli* K–12," *J. Bacteriol. 85*:1402–1408, Williams and Wilkins Co. (1963).

Potrykus, I. et al., "Molecular and general genetics of a hybrid foreign gene introduced into tobacco by direct gene transfer," *Mol. Gen. Genet. 199*:169–177, Springer–Verlag (1985).

Reich, T.J. et al., "Efficient Transformation of Alfalfa Protoplasts by the Intranuclear Microinjection of Ti Plasmids," *Bio/Technology 4*:1001–1004, Nature Publishing Co. (1986).

Slater, S. et al., "Metabolic engineering of Arabidopsis and Brassica for poly(3–hydroxybutyrate–co–3–hydroxyvalerate) copolymer production," *Nature Biotechnol. 17*:1011–1016, Nature Publishing Co. (Oct. 1999).

Tsuchida, T. and H. Momose, "Genetic Changes of Regulatory Mechanisms Occurred in Leucine and Valine Producing Mutants Derived from *Brevibacterium lactofermentum* 2256," *Agric. Biol. Chem. 39*:2193–2198, The Agricultural Chemical Society of Japan (1975).

Umbarger, H.E. and B. Brown, "Threonine Deamination in *Escherichia Coli,*" *J. Bacteriol. 73*:105–112, American Society for Microbiology (1957).

Valentin, H.E. et al., "PHA production, from bacteria to plants," *Int. J. Biol. Macromol. 25:* 303–306, Elsevier Science B.V. (Jun.–Jul. 1999).

Weising, K. et al., "Foreign Genes in Plants: Transfer, Structure, Expression, and Applications," *Ann. Rev. Genet. 22:* 421–477, Annual Review Inc. (1988).

Zhang, Y. et al., "Molecular Analysis and Characterization of a Broad–Host–Range Plasmid, pEP2," *J. Bacteriol. 176*:5718–5728, American Society for Microbiology (1994).

* cited by examiner

METHODS FOR PRODUCING L-ISOLEUCINE

CROSS REFERENCE TO RELATED APPLICATIONS

This application claims benefit to the filing dates of U.S. Provisional Application No. 60/142,071, filed Jul. 2, 1999; and U.S. Provisional Application No. 60/205,212, filed May 18, 2000; each of which is herein incorporated by reference in its entirety.

BACKGROUND OF THE INVENTION

1. Field of the Invention

The present invention relates, in general, to the field of production of amino acids. More specifically, the present invention relates to the over-production of isoleucine by nonhuman organisms.

2. Related Art

Corynebacteria have a long history of use in the industrial production of amino acids, which are used as food additives (most notably lysine and other essential amino acids) and as flavor enhancers (monosodium glutamate, or MSG). The overall global market for amino acids as animal feed additives is estimated to be worth more than $2 billion and totals about 700,000 metric tons of material. Lysine and methionine account for an overwhelming majority of the market, which also includes lower-volume products like threonine (Lessard, P. A., et al., "Corynebacteria, Brevibacteria," in *The Encyclopedia of Bioprocess Technology: Fermentation, Biocatalysis and Bioseparation*, John Wiley & Sons, New York, N.Y. (April 1999), Volume 2, pp. 729–740). The current production of isoleucine is less than 400 metric tons per year. This amino acid is currently used as a constituent of infusions and special dietary products. As with other amino acids the demand for isoleucine is increasing and its industrial production is expected to open up additional markets as an animal feed additive. Due to the tight control of isoleucine biosynthesis in bacteria, this amino acid is still in part produced commercially by direct extraction from protein hydrolysates.

The Gram positive *Corynebacterium glutamicum* is currently used in industry to produce over 100 grams of lysine per liter of culture. The flux of carbon through metabolic pathways can be diverted from the production of lysine to make other related amino acids by the processes and methods of metabolic engineering. Traditional metabolic manipulation involved random mutagenesis and screening for the desired changes in physiology, but transformation and genetic manipulation tools have been developed in the last ten years to allow more direct engineering of specific pathway elements in Corynebacterium (Jetten, M. S. M., et al., "Molecular organization and regulation of the biosynthetic pathway for aspartate-derived amino acids in *Corynebacterium glutamicum*," in *Industrial microorganisms: basic and applied molecular genetics*, Baltz, R. H., et al., eds., Am. Soc. Microbiol., Washington, D.C. (1993), pp. 97–104; Lessard, P. A., et al., "Corynebacteria, Brevibacteria," in *The Encyclopedia of Bioprocess Technology: Fermentation, Biocatalysis and Bioseparation*, John Wiley & Sons, New York, N.Y. (April 1999), Volume 2, pp. 729–740).

L-Isoleucine belongs to the aspartate-derived family of amino acids, as do lysine, homoserine, threonine and methionine. The enzymes that synthesize this family of amino acids have been well characterized in Corynebacterium, as has their regulation (FIG. 1). The first important regulatory point in the production of isoleucine by *C. glutamicum* is the end-product inhibition of the first committed enzyme, threonine dehydratase (E.C. 4.2.1.16), encoded by the gene ilvA. Overproduction of isoleucine has been accomplished by introducing excess threonine dehydratase (encoded by ilvA) into threonine producer strains (Colón, G. E., et al., *Appl. Microbiol. Biotechnol.* 43:482–488 (1995)). Threonine dehydratase is normally feedback inhibited by isoleucine. Mutant derivatives of threonine dehydratase with reduced sensitivity to isoleucine provided an additional dividend in this isoleucine production system (Hashiguchi, K., et al., *Biosci. Biotechnol. Biochem.* 61:105–108 (1997); Morbach, S. et al., *Appl. Env. Microbiol.* 61:4315–4320 (1995)). Despite these gains, it appears that amino acid export has been a serious limitation to the effectiveness of amino acid production (Kelle, R., et al., *J. Biotechnol.* 50:123–136 (1996)).

Work on artificial enzyme evolution has shown that it is difficult to subtly alter a task for which an enzyme was specifically evolved, while it is easier to coopt an enzyme for a completely new task (Benner, S. A., Chem. Rev. 89:789–806 (1989)).

One such alternative enzyme might be the catabolic threonine dehydratase, also called biodegradative threonine dehydratase, (E.C. 4.2.1.16), which is also known as threonine deaminase. This threonine dehydratase is produced in *E. coli* cells when the organism is grown anaerobically in a medium containing high concentrations of amino acids and no glucose (Umbarger, H. E. & Brown, B., *J. Bacteriol* 73:105–112 (1957)). In contrast to the threonine dehydratase encoded by ilvA, an anabolic threonine dehydratase, the enzyme encoded by tdcB in *E. coli* is insensitive to inhibition by L-isoleucine and is activated by adenosine 5'-monophosphate. The tdcB gene from *E.coli* has already been cloned and sequenced (Goss, T. J. & Datta, P., *Mol. Gen. Genet.* 201:308–314 (1985)).

In the past, overproduction of isoleucine has been accomplished by introduced excess threonine dehydratase encoded by ilvA, an anabolic threonine dehydratase, into threonine producer strains (colón, G. E., et al., *Appl. Microbiol. Biotechnol.* 43:482–488 (1995)). Although the conventional methods have considerably enhanced the production of isoleucine, the development of a more efficient, cost-effective technique is required in order to meet increasing demand for L-isoleucine.

BRIEF SUMMARY OF THE INVENTION

It is a general object of the invention to provide a method for over-producing L-isoleucine.

It is a specific object of the invention to provide a method for producing L-isoleucine comprising growing a transformed nonhuman organism under conditions that provide for synthesis of L-isoleucine, wherein said nonhuman organism comprises one or more copies of a transgene comprising at least one nucleotide sequence encoding catabolic threonine dehydratase, wherein said L-isoleucine is synthesized by said transformed nonhuman organism, said synthesis being greater than that of the corresponding non-transformed nonhuman organism, and recovering said L-isoleucine from said culture medium in which said transformed nonhuman organism was cultured.

It is a specific object of the invention to provide a method for producing L-isoleucine comprising growing an L-isoleucine producing nonhuman organism comprising one or more copies of a transgene comprising at least one nucleotide sequence encoding catabolic threonine dehydratase, wherein said nonhuman organism synthesizes L-isoleucine, said synthesis being greater than that of a corresponding nonhuman organism which does not comprise one or more copies of a transgene comprising at least one nucleotide sequence encoding catabolic threonine dehydratase, and recovering said L-isoleucine from said culture media in which said L-isoleucine producing nonhuman organism was cultured.

It is another specific object of the invention to provide a transformed non-human organism, wherein said transformed nonhuman organism is an L-isoleucine producing nonhuman organism, comprising one or more copies of a transgene comprising at least one nucleotide sequence encoding catabolic threonine dehydratase, wherein said transformed nonhuman organism synthesizes L-isoleucine, said synthesis being greater than that of the corresponding nontransformed nonhuman organism.

It is another object of the invention to provide an L-isoleucine producing nonhuman organism comprising one or more copies of a transgene comprising at least one nucleotide sequence encoding catabolic threonine dehydratase, wherein said nonhuman organism synthesizes L-isoleucine, said synthesis being greater than that of a corresponding nonhuman organism which does not comprise one or more copies of a transgene comprising at least one nucleotide sequence encoding catabolic threonine dehydratase.

It is another specific object of the invention to provide a transformed organism, *Corynebacterium glutamicum* ATCC21799 comprising pAPE7, ATCC deposit no. PTA-981. It is another specific object of the invention to provide a transformed organism, *Corynebacterium glutamicum* ATCC21799 comprising pAPE18, ATCC deposit no. PTA-978.

It is another specific object of the invention to provide an alpha-ketobutyrate producing nonhuman organism, comprising one or more copies of a transgene comprising at least one nucleotide sequence encoding catabolic threonine dehydratase and, additionally one or more transgenes comprising at least one nucleotide sequence encoding one or more enzymes involved in L-threonine biosynthesis, wherein said transformed nonhuman organism synthesizes alpha-ketobutyrate, said synthesis being greater than that of a corresponding non-transformed nonhuman organism.

It is another specific object of the invention to provide a plant, or plant part thereof comprising one or more copies of a transgene comprising at least one nucleotide sequence encoding catabolic threonine dehydratase.

It is another specific object of the invention to provide a plant, or plant part thereof, wherein said plant or said part thereof, comprises one or more copies of a transgene comprising at least one nucleotide sequence encoding catabolic threonine dehydratase, wherein said plant or plant part thereof retains more threonine dehydratase enzyme activity during, or after, contacting herbicide than a corresponding plant, or plant part thereof, contacted with said herbicide, which does not comprise one or more copies of a transgene comprising at least one nucleotide sequence encoding catabolic threonine dehydratase.

It is another specific object of the invention to provide a method of producing a plant, or part thereof, wherein said plant, or plant part thereof, is contacted with one or more copies of a transgene comprising at least one nucleotide sequence encoding catabolic threonine dehydratase, and wherein said plant, or part thereof, after said contacting comprises detectable transgene.

It is another specific object of the invention to provide a method of using the plant, or plant part thereof, wherein said plant, or plant part thereof, is cultivated in the presence of an herbicide and wherein growth of said plant, or said part thereof, is greater than the growth of a corresponding plant, or plant part thereof, contacted with said herbicide, which does not comprise one or more copies of a transgene comprising at least one nucleotide sequence encoding catabolic threonine dehydratase.

It is another specific object of the invention to provide a method of enhancing resistance to an herbicide in a plant, or plant part thereof, said method comprising introducing into said plant, or plant part thereof, one or more copies of a transgene comprising at least one nucleotide sequence encoding catabolic threonine dehydratase.

Further object and advantages of the present invention will be clear from the description that follows.

DEFINITIONS

Figure 1:
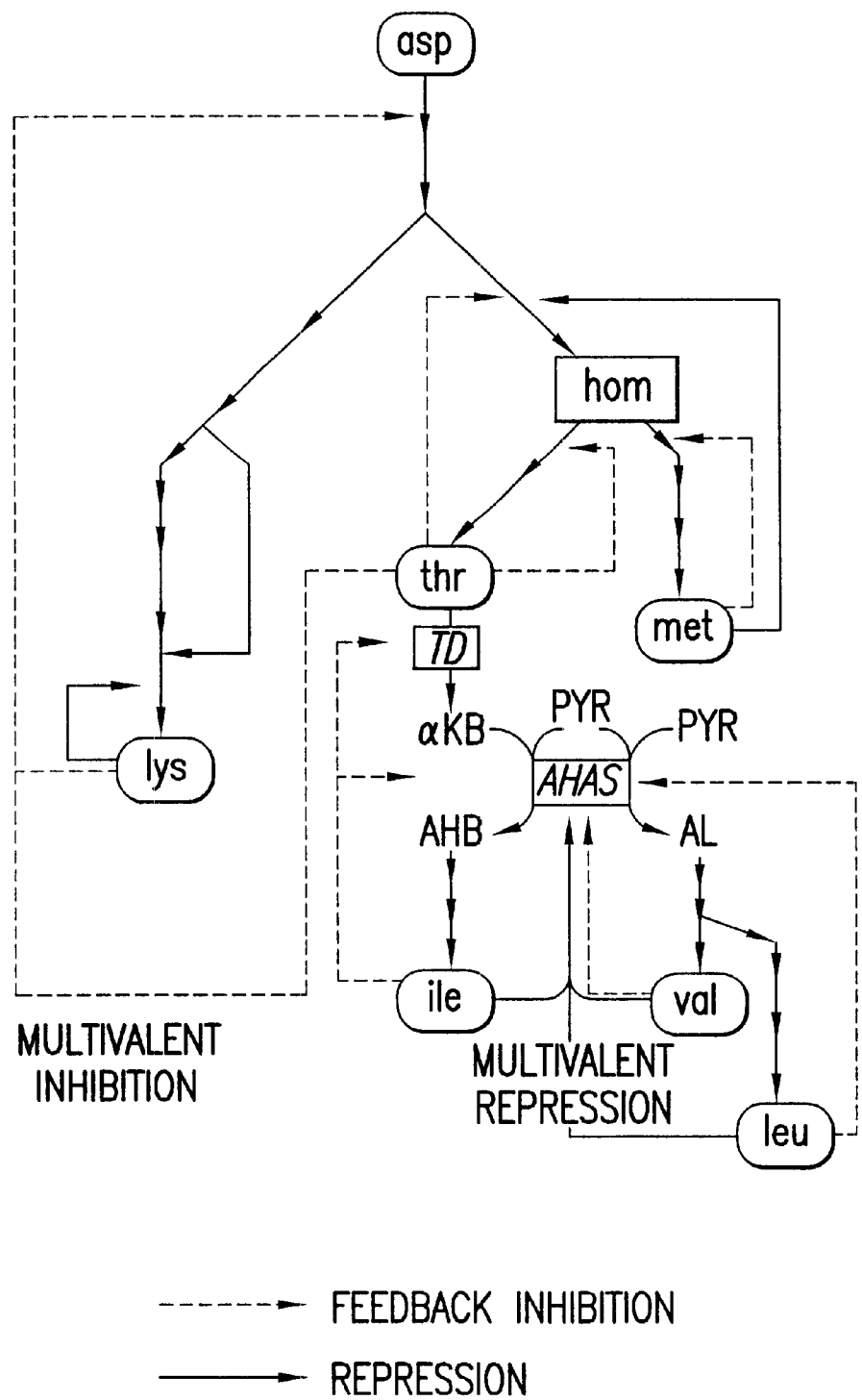
FIG. 1. Aspartate-derived amino acids pathway. Asp, aspartic acid; hom, homoserine; thr, threonine; met, methionine; lys, lysine; ile, isoleucine; val, valine; leu, leucine; alpha-KB, alpha ketobutyrate; AHB, acetohydroxybutyric acid; PYR, pyruvate; AL, acetolactate; AHAS, acetohydroxyacid synthase; TD, threonine dehydratase.

In the description that follows, a number of terms used in recombinant DNA (rDNA) are extensively utilized. In order to provide a clear and consistent understanding of the specification and the claims, the following definitions are provided.

Catabolic threonine dehydratase. As used herein, "catabolic threonine dehydratase" refers to threonine dehydratase enzymes which are directed to the breakdown of threonine in the nonhuman organism. Catabolic threonine dehydratase enzymes catalyze the conversion of threonine into alpha-ketobutyrate and ammonia. Catabolic threonine dehydratase is also known as threonine deaminase. Catabolic threonine dehydratases are not inhibited by isoleucine to the same extent as are the biosynthetic threonine dehydratase enzymes and retain more of their activity even as the cells accumulate isoleucine. In the invention, "catabolic threonine dehydratase" refers to catabolic threonine dehydratase (E.C.4.2.1.19; formerly E.C.4.2.1.16) as well as to a catabolic threonine dehydratase isolated and purified from any source, which is encoded by the same, or substantially identical, nucleotide sequence as catabolic threonine dehydratase (E.C.4.2.1.19).

Control sequence. As used herein, "control sequence" refers to a DNA sequence or sequences necessary for the expression or regulation (transcriptional or translational) of an operably linked coding sequence in a particular nonhuman organism. The control sequences which are suitable include, for example, a promoter, optionally an operator sequence, a ribosome binding site, and a transcription terminator. Many other sequences such as enhancers, silencers and promoters are known in the art. See, for example, U.S. Pat. Nos. 4,980,285; 5,631,150; 5,759,828; 5,888,783 and, 5,919,670.

Feedback insensitive or feedback resistant. As used herein, the terms are used to denote enzymes (or the genes encoding them) that maintain the same or similar primary metabolic activity associated with a "wild-type" or native enzyme but whose regulatory properties have been modified (through directed mutation or random mutation) or whose enzymatic regulation is markedly different from that of the original enzymes(s). For example, while threonine dehydratase encoded by ilvA has much reduced activity in the presence of high levels of isoleucine, tdcB encodes a feedback insensitive threonine dehydratase that maintains more of its enzymatic activity in the presence of isoleucine. Another example is that the homoserine dehydrogenase encoded by hom can be inhibited by threonine, whereas the homoserine dehydrogenase encoded by $hom^{dr}$ (a modified version of the same gene) retains much more of its activity in the presence of this metabolite.

Genetic elements. As used herein, "genetic elements" refers to defined nucleic acids (generally DNA or RNA) having expressible coding sequences for products such as proteins, apoproteins, or antisense nucleic acid constructs, which can perform or control pathway enzymatic functions. The expressed proteins can function as enzymes, repress or derepress enzyme activity, or control expression of enzymes. The nucleic acids encoding these expressible sequences can be either chromosomal, e.g. integrated into a nonhuman organism's chromosome by homologous recombination, transposition, or some other method, or extrachromosomal (episomal), e.g. carried by plasmids, cosmids, etc. Genetic elements include control elements. Many other genetic elements are known in the art. See, for example, U.S. Pat. Nos. 4,980,285; 5,631,150; 5,759,828; 5,888,783 and, 5,919,670.

Genetic manipulation. As used herein, the term "genetic manipulation" refers to the purposeful alteration of polynucleotide sequences either by in vitro techniques, in vivo techniques, or a combination of both in vitro and in vivo techniques. "Genetic manipulation" includes the introduction of heterologous polynucleotide sequences into nonhuman organisms, either into the chromosome or as extrachromosomally replicating elements, the alteration of chromosomal polynucleotide sequences, the addition and/or replacement of transcriptional and/or translational regulatory signals to chromosomal or plasmid encoded genes, and the introduction of various insertion, deletion and replacement mutations in genes of interest. Methods for in vitro and in vivo genetic manipulations are widely known to those skilled in the art. See, for example, Sambrook et al., *Molecular Cloning: A Laboratory Manual*, 2nd Ed., Cold Spring Harbor Press (1989) and U.S. Pat. Nos. 4,980,285; 5,631,150; 5,759,828; 5,888,783 and, 5,919,670.

Operably linked. As used herein, "operably linked" refers to a juxtaposition such that the normal function of the components can be performed. Thus, a coding sequence "operably linked" to control sequences refers to a configuration wherein the coding sequences can be expressed under the control of these sequences. Such control may be direct, that is, a single gene associated with a single promoter, or indirect, as in the case where a polycistronic transcript is expressed from a single promoter. See, for example, U.S. Pat. Nos. 4,980,285; 5,631,150; 5,707,828; 5,759,828; 5,888,783 and, 5,919,670, and Sambrook et al., *Molecular Cloning: A Laboratory Manual*, 2nd Ed., Cold Spring Harbor Press (1989).

Over-expression and Over-Production. As used herein, "over-expression" refers to gene expression. Genes and gene products can be overexpressed. Such gene products include RNAs, proteins and enzymes. On the other hand, "overproduce" refers to cellular products that accumulate, especially cell products that are to be harvested for some specific use. Thus proteins, materials (such as polymers), and metabolites (such as amino acids) are overproduced. Proteins may be either overexpressed (if referring to the control of gene expression) or overproduced (if referring to the accumulation of the proteins). By "over production" of L-isoleucine, it is intended that a nonhuman organism "over producing" L-isoleucine produces more molecules of L-isoleucine for each nonhuman organism under a given set of growth conditions than a similar nonhuman organism not "over producing" L-isoleucine.

Plant. As used herein, the term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous. See, U.S. Pat. Nos. 5,942,662; 5,990,390; and 5,994,622.

Promoter. As used herein, the term "promoter" has its art-recognized meaning, denoting a portion of a gene containing DNA sequences that provide for the binding of RNA polymerase and initiation of transcription. Promoter sequences are commonly, but not always, found in the 5' non-coding regions of genes. Sequence elements within promoters that function in the initiation of transcription are often characterized by consensus nucleotide sequences. Useful promoters include constitutive and inducible promoters. Many such promoter sequences are known in the art. See, for example, U.S. Pat. Nos. 4,980,285; 5,631,150; 5,707,828; 5,759,828; 5,888,783; 5,919,670, and, Sambrook et al.,

*Molecular Cloning: A Laboratory Manual*, 2nd Ed., Cold Spring Harbor Press (1989). Other useful promoters include promoters which are neither constitutive nor responsive to a specific (or known) inducer molecule. Such promoters may include those that respond to developmental cues (such as growth phase of the culture or stage of cell differentiation), or environmental cues (such as pH, osmoticum, heat, or cell density). A heterologous promoter is a promoter which is not naturally linked to the gene. Heterologous promoters may be from the same or different species. For example, a heterologous promoter may be a promoter from the same organism as the gene but naturally found linked to a different gene.

As used herein, a "plant promoter" is a promoter capable of initiating transcription in plant cells. "Plant promoter" has its art-recognized meaning, denoting a portion of a gene containing DNA sequences that provide for the binding of RNA polymerase and initiation of transcription. For example, for overexpression, a plant promoter fragment may be employed which will direct expression of the gene in all tissues of a regenerated plant. Such promoters are "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Alternatively, the plant promoter may an "inducible" promoter. Examples of environmental conditions that may effect transcription by inducible promoters include anaerobic conditions, elevated temperature, or the presence of light. Examples of promoters under developmental control include promoters that initiate transcription only in certain tissues, such as fruit, seeds, flowers, or ovules. Examples include the AP2 promoter, a promoter from the ovule-specific BEL1 gene promoter. See, for example, U.S. Pat. Nos. 5,942,662; 5,990,390; and 5,994,622.

Transformed nonhuman organisms. As used herein, the term "transformed nonhuman organisms" includes the primary transformed subject cell and its transformed progeny. The nonhuman organism may be prokaryotic or eukaryotic. Thus "transformants" or "transformed cells" includes the primary subject cell, transformed with the transgene, and cultures derived therefrom, without regard for the number of transfers. It is also understood that all progeny may not be precisely identical in DNA content, due to deliberate or inadvertent mutations and/or modifications. Mutant progeny which have the same functionality as screened for in the originally transformed cell are included. Where distinct designations are intended, it will be clear from the context. See, for example, U.S. Pat. Nos. 4,980,285; 5,631,150; 5,707,828; 5,759,828; 5,888,783; 5,919,670, and, Sambrook et al., *Molecular Cloning: A Laboratory Manual*, 2nd ed., Cold Spring Harbor Press (1989).

Transgene. As used herein, the term "transgene" when used in reference to polynucleotide sequences, refers to polynucleotide sequences not naturally present in a cell. Thus the term "transgene" includes, for example, the promoter of gene A operably joined to structural gene B, when A and B genes are from the same organism, as well as the case in which a polynucleotide sequence of one species is transferred to a cell of a different species (or strain). The term "transgene" also includes clones of transgenes which have been so modified. See, U.S. Pat. Nos. 4,980,285; 5,631,150; 5,707,828; 5,759,828; 5,888,783 and, 5,919,670.

Transgenic Plant. As used herein, the term "transgenic plant" refers to plants having a genome which has been augmented by at least one incorporated DNA sequence. Such DNA sequences include but are not limited to genes which are not normally present, DNA sequences not normally transcribed into RNA or translated into a protein ("expressed"), or any other genes or DNA sequences which are introduced into the non-transformed plant. Included genes are genes which may normally be present in the non-transformed plant but which one desires to either genetically engineer or alter the expression. The genome of transgenic plants of the present invention will haste been augmented through the stable introduction of the transgene, or. the introduced transgene will replace an endogenous sequence. See U.S. Pat. No. 5,994,622. The term may additionally include "transient" forms of gene expression to alter plants, i.e., without permanently altering the genome. Such methods may be accomplished by virus-based gene expression vectors to introduce genes episomally. Episomally maintained genes affect gene expression but do not alter the genome.

Vector. As used herein, the term "vector" refers to a polynucleotide sequence suitable for transferring transgenes into a host cell. Host cells may be plant cells, prokaryotic cells or eukaryotic cells. The term may include plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al., *Molecular Cloning: A Laboratory Manual*, 2nd Ed., Cold Spring Harbor Press (1989).

DETAILED DESCRIPTION OF THE INVENTION

The disclosed invention relates to nonhuman organisms which express a catabolic threonine dehydratase.

An object of the present invention is to provide an efficient and cost-effective method for synthesizing L-isoleucine by enhancing the capability of a nonhuman organism, such as bacterium, to produce L-isoleucine. It is a further object of the present invention to provide methods for constructing transformed nonhuman organisms, and the transformed nonhuman organisms, thereby constructed. The transformed nonhuman organisms over-produce L-isoleucine. The transformed nonhuman organisms also over-express heterologous catabolic threonine dehydratase. In one embodiment, the nonhuman organism used in the invention belongs to the genus Corynebacterium. In a preferred embodiment, the nonhuman organism is *Corynbacterium glutamicum*. In a particularly preferred embodiment, the nonhuman organism is *Corynbacterium glutamicum* ATCC 21799. In one embodiment, the transformed nonhuman organism is of the genus Escherichia. In another embodiment, the transformed nonhuman organism is *Escherichia coli*. In a preferred embodiment, the transgene comprises a tdcB gene from *E. coli*.

The transformed nonhuman organisms of the present invention can secrete the synthesized L-isoleucine into the culture medium. This goal is achieved through modification of the metabolism of a desired nonhuman organism by introducing and expressing desired transgenes. This goal is also achieved by further modification of the metabolism of certain genes endogenous to such nonhuman organisms in their native state.

It is an object of the invention to provide a method for producing L-isoleucine comprising growing a transformed nonhuman organism under conditions that provide for synthesis of L-isoleucine, wherein said nonhuman organism comprises one or more copies of a transgene comprising at least one nucleotide sequence encoding catabolic threonine dehydratase, wherein said L-isoleucine is synthesized by said transformed nonhuman organism, said synthesis being greater than that of a corresponding non-transformed nonhuman organism, and recovering said L-isoleucine from said culture media in which said transformed nonhuman organism was cultured.

In one embodiment, the transformed nonhuman organism additionally over-produces one or more of L-lysine, L-methionine, L-leucine, L-valine, L-threonine, L-aspartic acid, or homoserine, wherein said production is greater than that of a corresponding, nontransformed nonhuman organism. In one embodiment, the transformed nonhuman organism is of the genus Corynebacterium. In another embodiment, the nonhuman organism is *Corynebacterium glutamicum*. In a preferred embodiment, the nonhuman organism is *Corynebacterium glutamicum* is ATCC 21799.

In one embodiment, the transgene comprises a tdcB gene from *E. coli*. In another embodiment, the transgene comprises a tdcB gene encoding catabolic threonine dehydratase (E.C.4.2.1.19). In another embodiment, the transgene comprises a catabolic threonine dehydratase gene from *Salmonella typhimurium*. In a preferred embodiment, the nonhuman organism is transformed with pAPE7. In a highly preferred embodiment, the nonhuman organism is *Corynebacterium glutamicum* and the transgene comprises a tdcB gene from *E. coli*.

In one embodiment of the invention, conditions that provide for synthesis of L-isoleucine comprise supplementation of culture media with one or more amino acids or amino acid precursors. In another embodiment, one or more amino acids or amino acid precursors is one or more of L-methionine, L-leucine, L-valine, L-threonine, L-lysine, L-aspartic acid, glycine, L-alanine and homoserine.

In another embodiment of the method for producing L-isoleucine, the nonhuman organism additionally comprises one or more transgenes comprising at least one nucleotide sequence encoding one or more enzymes involved in L-isoleucine biosynthesis. In a preferred embodiment, one or more enzymes involved in L-isoleucine biosynthesis is one or more of homoserine dehydrogenase, homoserine kinase, acetohydroxy acid synthase, aspartokinase, aspartate, β-semialdehyde dehydrogenase, threonine synthase, acetohydroxy acid isomeroreductase, dihydroxy acid dehydratase, feedback insensitive forms of any of the preceeding enzymes, and any combination thereof.

In one embodiment of the method for producing L-isoleucine, the method comprises growing an L-isoleucine producing nonhuman organism comprising one or more copies of a transgene comprising at least one nucleotide sequence encoding catabolic threonine dehydratase, wherein said nonhuman organism synthesizes L-isoleucine, said synthesis being greater than that of a corresponding nonhuman organism which does not comprise one or more copies of a transgene comprising at least one nucleotide sequence encoding catabolic threonine dehydratase and recovering said L-isoleucine from said culture media in which said L-isoleucine producing nonhuman organism was cultured. In a preferred embodiment of the method the nonhuman organism has been genetically manipulated to overproduce one or more of L-lysine, L-methionine, L-leucine, L-valine, L-threonine, L-aspartic acid, and homoserine prior to the introduction of said nucleotide sequence encoding catabolic threonine dehydratase into said nonhuman organism. In a highly preferred embodiment, the nonhuman organism comprises hom$^{dr}$ and thrB and overproduces threonine.

It is another object of the invention to provide an L-isoleucine producing nonhuman organism comprising one or more copies of a transgene comprising at least one nucleotide sequence encoding catabolic threonine dehydratase, wherein said non human organism synthesizes L-isoleucine, said synthesis being greater than that of the corresponding non-transformed nonhuman organism. In one embodiment, the nonhuman organism over-produces L-lysine, L-methionine, L-leucine, L-valine, L-threonine, L-aspartic acid, and homoserine prior to the introduction of said one or more copies of said transgene. In another embodiment, the transgene comprises a catabolic threonine dehydratase gene from *E. coli* or from *Salmonella typhimurium*. In a preferred embodiment, the transgene comprises a tdcB gene encoding catabolic threonine dehydratase (E.C.4.2.1.19). In one embodiment, the nonhuman organism is of the genus Corynebacterium. In another embodiment, the nonhuman organism is *Corynebacterium glutamicum*. In a preferred embodiment, the nonhuman organism *Corynebacterium glutamicum* is ATCC 21799. In one embodiment, the nonhuman organism is of the genus Escherichia. In another embodiment, the nonhuman organism is *Escherichia coli*.

In another embodiment of the invention, the transformed nonhuman organism additionally comprises one or more transgenes comprising at least one nucleotide sequence encoding one or more enzymes involved in L-isoleucine biosynthesis. In a preferred embodiment, one or more enzymes involved in L-isoleucine biosynthesis is one or more of homoserine dehydrogenase, homoserine kinase, acetohydroxy acid synthase, aspartokinase, aspartate β-semialdehyde dehydrogenase, threonine synthase, acetohydroxy acid isomeroreductase, dihydroxy acid dehydratase, feedback insensitive forms of any of the preceeding enzymes, and any combination thereof.

It is another object of the invention to provide an L-isoleucine producing nonhuman organism comprising one or more copies of a transgene comprising at least one nucleotide sequence encoding catabolic threonine dehydratase, wherein said nonhuman organism synthesizes L-isoleucine, said synthesis being greater than that of a corresponding nonhuman organism which does not comprise one or more copies of a transgene comprising at least one nucleotide sequence encoding catabolic threonine dehydratase. In one embodiment, the nonhuman organism has been genetically manipulated to overproduce one or more of L-lysine, L-methionine, L-leucine, L-valine, L-threonine, L-aspartic acid, and homoserine prior to the introduction of said nucleotide sequence encoding catabolic threonine dehydratase into said nonhuman organism. In a preferred embodiment, the nonhuman organism comprises hom$^{dr}$ and thrB and overproduces threonine.

It is a further object of the invention to provide *Corynebacterium glutamicum* ATCC 21799 transformed with pAPE7, ATCC deposit no. PTA-981. It is another object of the invention to provide *Corynebacterium glutamicum* ATCC 21799 transformed with pAPE18, ATCC deposit no. PTA-978.

It is a further object of the invention to provide an alpha-ketobutyrate producing nonhuman organism, comprising one or more copies of a transgene comprising at least one nucleotide sequence encoding catabolic threonine dehydratase, and, additionally one or more transgenes comprising at least one nucleotide sequence encoding one or more enzymes involved in L-threonine biosynthesis, wherein said transformed nonhuman organism synthesizes alpha-ketobutyrate, said synthesis being greater than that of a corresponding non-transformed nonhuman organism. In one embodiment of the invention, the nonhuman organism further synthesizes one or more polymers selected from the group consisting of polyhydroxyalkanoates (PHAs), polyhydroxybutyrate (PHB), and poly-hydroxybutyrate-co-valerate (PHBV), and wherein said polymers are accumulated intracellularly or secreted.

It is another object of the invention to provide a plant, or plant part thereof, comprising one or more copies of a transgene comprising at least one nucleotide sequence encoding catabolic threonine dehydratase.

It is another object of the invention to provide a plant, or plant part thereof, wherein said plant or said part thereof, comprises one or more copies of a transgene comprising at least one nucleotide sequence encoding catabolic threonine dehydratase, wherein said plant or plant part thereof, retains more threonine dehydratase enzyme activity after contacting herbicide than a corresponding plant, or plant part thereof, contacted with said herbicide, which does not comprise one or more copies of a transgene comprising at least one nucleotide sequence encoding catabolic threonine dehydratase. In one embodiment, the plant, or part thereof, is selected from leaves, roots, stems, flowers and flower parts, seeds, pollen, cells and calli. In one embodiment, the plant, or part thereof, retains resistance to a herbicide wherein said herbicide comprises an L-isoleucine analog. In a preferred embodiment, the plant, or part thereof, produces alpha-ketobutyrate and/or isoleucine before contact with, in the presence of, and after said contact with said herbicide.

It is another object of the invention to provide a method of producing a plant, or part thereof, wherein said plant, or plant part thereof, is contacted with one or more copies of a transgene comprising at least one nucleotide sequence encoding catabolic threonine dehydratase, and wherein said plant, or part thereof, after said contacting, comprises detectable transgene.

It is another object of the invention to provide a method of using a plant, or plant part thereof, wherein said plant, or plant part thereof, is cultivated in the presence of an herbicide and wherein growth of said plant, or said part thereof, is greater than the growth of a corresponding plant, or plant part thereof. contacted with said herbicide, which does not comprise one or more copies of a transgene comprising at least one nucleotide sequence encoding catabolic threonine dehydratase.

It is another object of the invention to provide a method of enhancing resistance to an herbicide in a plant, or plant part thereof, said method comprising introducing into said plant, or plant part thereof, one or more copies of a transgene comprising at least one nucleotide sequence encoding catabolic threonine dehydratase.

It is further an object of the invention to provide a method for the production of L-isoleucine by utilizing a novel metabolic pathway as above, wherein said pathway modifies the pathways of L-isoleucine biosynthesis and/or metabolism. In this invention, the pathway is modified so that the transformed nonhuman organism now produces L-isoleucine by a redirection of the carbon flux from the lysine pathway to the isoleucine pathway.

It is further an object of the invention to provide a method for the production of L-isoleucine by augmenting the pre-existing L-isoleucine pathway. The production of L-isoleucine is accomplished by the introduction and overexpression of the genes coding for catabolic threonine dehydratase into an L-isoleucine producing nonhuman organism. In another embodiment of the invention, the L-isoleucine producing nonhuman organism additionally overproduces L-lysine.

It is further an object of the invention to provide a method for the production of L-isoleucine using the transformed nonhuman organism as above, the method using the altered L-isoleucine pathway above, such pathway being altered further by inactivating, using chemically induced mutagenesis or gene disruption of one or more genes encoding any of the enzymes involved in the biosynthesis of L-amino acids. In one embodiment of the invention, the inactivated genes are involved in the biosynthetic reactions which produce L-isoleucine.

In another object of the invention, over production of L-isoleucine is achieved by inserting a transgene which comprises a nucleotide sequence coding for an enzyme which is utilized on the route of biosynthesis of an L-amino acid product into a first vector, and inserting a second transgene, which comprises a nucleotide sequence which codes for an enzyme different from said first enzyme on the route of biosynthesis of said L-amino acid into a second vector. The vectors are then introduced into a strain of a nonhuman organism to transform said strain which is capable of producing said L-amino acid, wherein the enzymes are highly rate determining enzymes for the biosynthesis of said L-amino acid. Further, insertion of the first and second transgenes may optionally be followed by insertion of one or more additional transgenes wherein the additional transgenes are also highly rate determining enzymes for the biosynthesis of said L-amino acid.

Any strain of nonhuman organism capable of producing L-amino acids is useful in the practice of this invention. Such strains include strains lacking a catabolic threonine dehydratase, strains expressing ineffective levels of catabolic threonine dehydratase enzymes under specific conditions (enzyme expression under anaerobic conditions, but little or no expression under aerobic conditions, such as in *E. coli*, for example), strains expressing low levels of catabolic threonine dehydratase enzymes under typical growth conditions and strains expressing high levels of catabolic threonine dehydratase.

The first two enzymes in the threonine to isoleucine pathway (threonine dehydratase and acetohydroxyacid synthase) have been found to be important in isoleucine biosynthesis. Threonine dehydratase is sensitive to feedback inhibition by isoleucine and therefore this can be a limiting factor for the improvement of isoleucine biosynthesis. AHAS (acetohydroxyacid synthase) is also feedback inhibited by isoleucine but it has been shown to be highly inducible in the presence of its substrate, alpha-ketobutyrate (colón, G. E., et al., *Appl. Microbiol. Biotechnol.* 43:482–488 (1995); Eggeling, L., et al., *Appl. Microbiol. Biotechnol.* 25:346–351 (1987)). Therefore threonine dehydratase has been preferred as a target for metabolic engineering to increase carbon flux into the isoleucine pathway.

The tdcB gene of *E. coli* encoding catabolic threonine dehydratase has been cloned and inserted in an expression vector for *C. glutamicum*. The tdcB gene was expressed in two different strains of *Corynebacterium glutamicum*, AS019-E12 and ATCC 21799. In vitro enzymatic assays showed that the catabolic threonine dehydratase expressed in *Corynebacterium glutamicum* retained its insensitivity to isoleucine. A concentration of 200 mM isoleucine resulted in only a 40% inhibition of the catabolic threonine dehydratase whereas just 15 mM isoleucine was able to completely inhibit the native threonine dehydratase in the ATCC 21799 strain. Accordingly, Morbach S., et al., *Appl. Environ.*

Microbiol. 61:4315–4320 (1995), found a complete inhibition of the endogenous threonine dehydratase (encoded by ilvA) with a concentration of 5 mM isoleucine in *Corynebacterium glutamicum* MH20-22B. Some authors have obtained deregulated threonine dehydratase by generating mutations in the ilvA gene (Hashiguchi, K., et al., *Biosci. Biotechnol. Biochem.* 61:105–108 (1997); Mockel, B., et al., *Mol. Microbiol.* 13:833–842 (1994)). Theirmutatedthreonine dehydratase V323A had 22% activity at 50 mM isoleucine (Morbach, S., et al., *Appl. Environ. Microbiol.* 61:4315–4320(1995)) whereas the catabolic threonine dehydratase of *E. coli* has still 70–80% activity at an identical isoleucine concentration. These results show the potential for using the catabolic threonine dehydratase of *E. coli* in Corynebacterium.

To determine whether expressing the catabolic threonine dehydratase (tdcB gene) had any greater benefit in isoleucine production when compared to overexpression of the native enzyme, encoded by ilvA, two overexpression vectors were constructed, one carrying the ilvA gene, the other carrying the tdcB gene. These plasmids were introduced into a lysine producing strain, ATCC 21799, a strain whose feedback-resistant aspartokinase permits high lysine production (Jetten, M. S. M., et al., *Appl. Microbiol. Biotechnol.* 43:76–82 (1995)). The results showed that 20-fold overexpression of the ilvA gene product, threonine dehydratase, led to a 4-fold increase in the isoleucine production ($0.2\ g \cdot l^{-1}$). This low yield can be explained by a reduction in activity of the threonine dehydratase due to the feedback inhibition by isoleucine and/or by the inhibiting effect of leucine added in the medium. ATCC 21799 is a leucine auxotroph requiring the inclusion of leucine in the medium. However, the excess leucine may be decreasing the activity of acetohydroxy acid synthase (AHAS), the second enzyme of the isoleucine pathway, via feedback inhibition (Eggeling, L., et al., *Appl. Microbiol Biotechnol.* 25:346–351 (1987)). AHAS has been indeed found to be inhibited by leucine and valine, and its expression is repressed multivalently by all three branched-chain amino acids (Eggeling, L., et al., *Appl. Microbiol. Biotechnol.* 25:346–351 (1987); Tsuchida, T. & Momose, H., *Agric. Biol. Chem.* 39:2193–2198 (1975)). In comparison, 15-fold overexpression of the catabolic threonine dehydratase led to a significant 50-fold increase in the isoleucine production ($2.5\ g \cdot l^{-1}$) at the expense of lysine production ($1.4\ g \cdot l^{-1}$). This observation eliminates the possibility that leucine-inhibition of AHAS enzyme was responsible for low isoleucine yield in the ilvA overexpressing strain, since excess leucine was included in the tdcB expressing cultures as well.

Figure 7A:
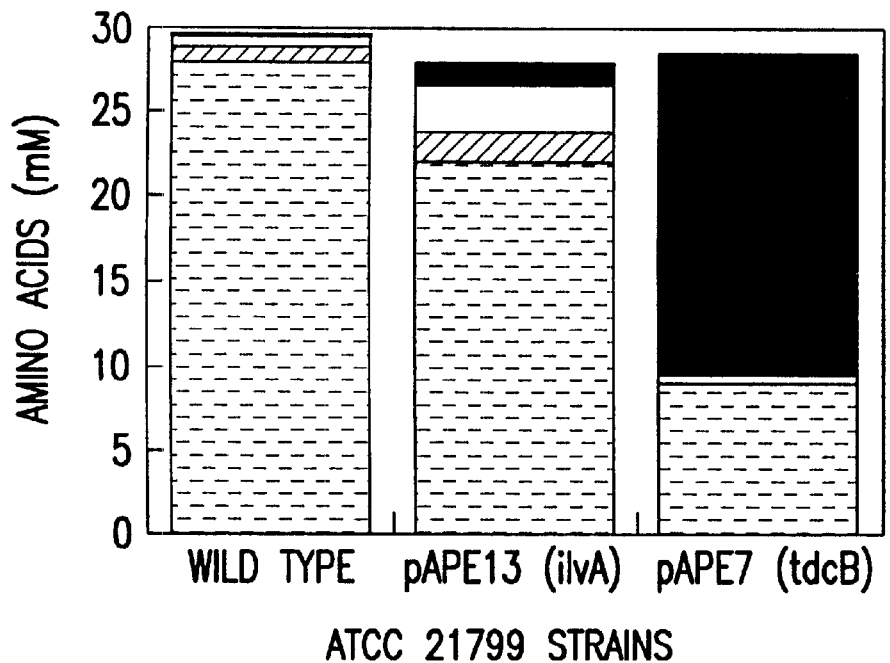
FIGS. 7A, 7B. Amino acids (7A) and carbon balance (7B) for the three strains calculated from final fermentation titers. Lysine and isoleucine carbon was multiplied by ⅔ to account for pyruvate contribution in their respective branches. Alanine carbon was multiplied by ¾ to account for the economy of 1 mole of $CO_2$ comparatively to the amino acids of the aspartate-derived pathway.
Figure 7B:
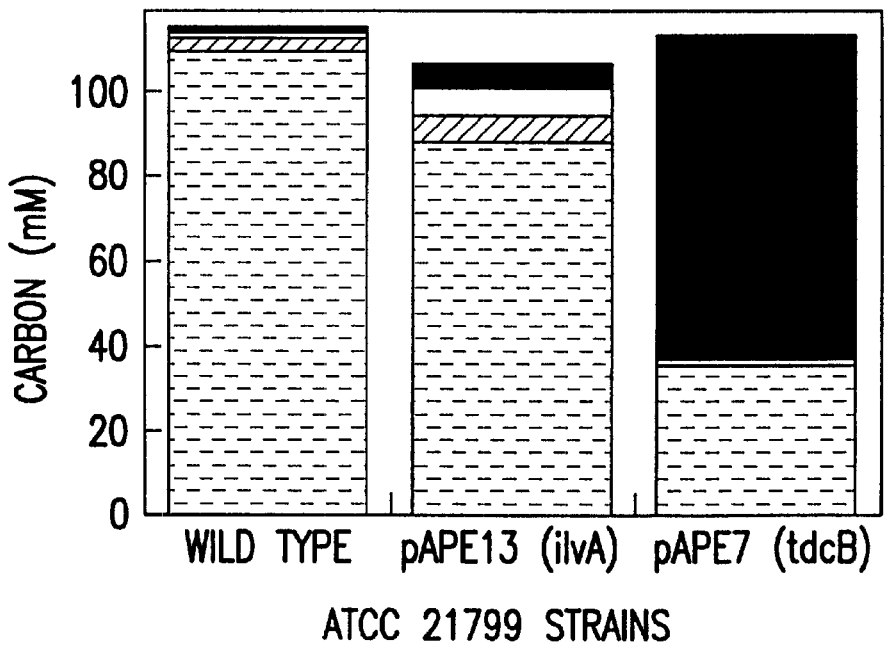
Figure 8:
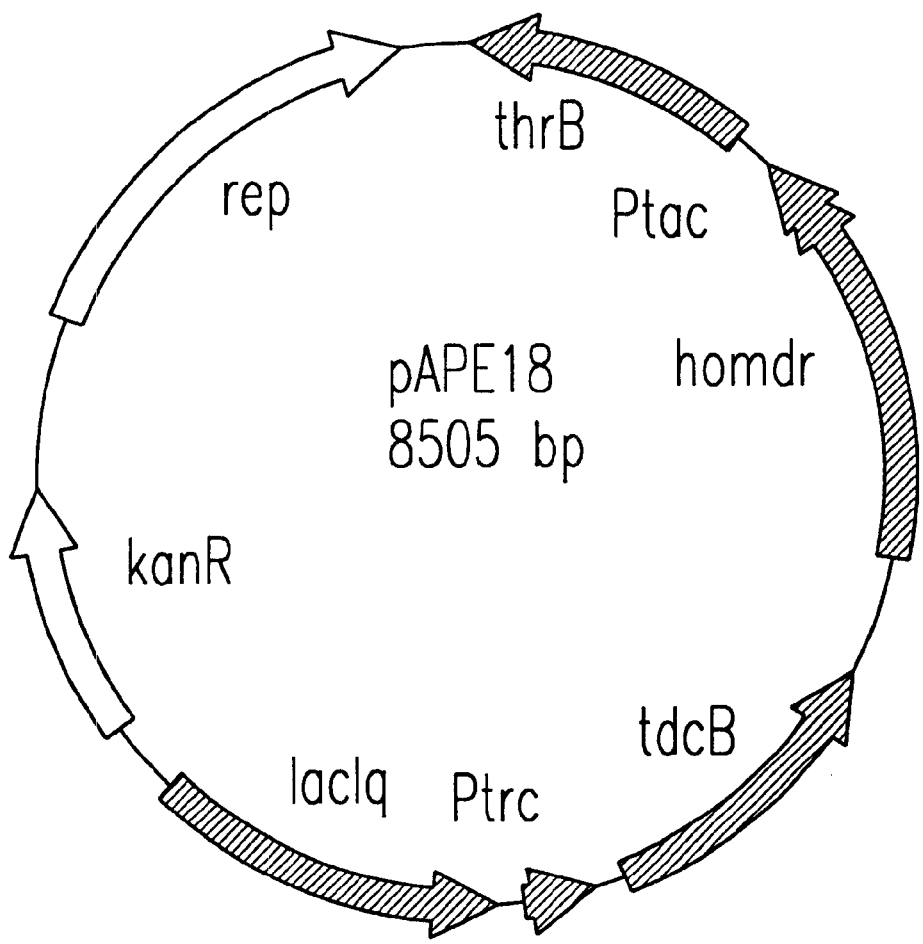
FIG. 8: Plasmid Map of pAPE18. Plasmid carrying tdcB gene under control of the trc promoter (Ptrc); a deregulated homoserine dehydrogenase ($hom^{dr}$); and the homoserine kinase gene (thrB) under control of the tac promoter (Ptac); kanR=kanamycin resistance gene; rep=NG2 rep gene.

In order to determine the distribution of the carbon throughout the aspartate-derived amino acid pathway in the different strains, amino acid and carbon balances in the amino acid pathways were compared in the three strains (FIG. 7). The carbon balances have been corrected to account for incorporation of 1 mole of pyruvate into the lysine and isoleucine pathways and for the economy of 1 mole of $CO_2$ for the synthesis of alanine, and thus represent only derivatives of the carbon skeleton of aspartate. The three strains produced comparable amount of amino acids. In the ilvA overexpressing strain, only 5% of the carbon available for the aspartate-derived amino acids pathway was directed to isoleucine and 75% into lysine. A higher concentration of homoserine and alanine was produced in this strain. While applicants do not wish to be limited by any single explanation, this result can be explained by the fact that an increase of homoserine concentration at the expense of lysine (as a result of ilvA overexpression) leads to a higher availability of pyruvate that can be converted into alanine.

The balances show that in the strain carrying the plasmid containing the tdcB gene the carbon flux has been redirected from the lysine pathway through the isoleucine pathway. In this strain, 70% of the carbon available for the aspartate-derived amino acids pathway has been converted into isoleucine. As a comparison, colón, G. E., et al., Appl. Microbiol. Biotechnol. 43:482–488 (1995), found that 80% of the carbon available for the aspartate-derived amino acids pathway has been converted to isoleucine in an ilvA overexpressing ATCC 21799 strain, but in that case they used a threonine overproducing strain as the host for ilvA overexpression. Thus, this host strain also overexpressed a deregulated homoserine dehydrogenase ($hom^{dr}$) and the homoserine kinase (thrB). The present study demonstrates that overexpression of tdcB alone in a lysine producing strain is sufficient to drive isoleucine overproduction to a level comparable to that demonstrated with a three-gene system ($hom^{dr}$, thrB, ilvA).

Growth kinetics showed that the strain carrying the plasmid containing the tdcB gene grew more slowly than the wild type or the ilvA overexpressing strains. This could be explained by a depletion of one or more amino acids, a consequence of the redirection of the carbon flux after expression of the tdcB gene. The inhibitory effect of alpha-ketobutyrate on the growth of *Corynebacterium glutamicum* has been already reported (Eggeling, L., et al., *Appl. Microbiol. Biotechnol.* 25:346–351 (1987)). Addition of a mixture of amino acids from a casein hydrolysate to the medium reestablished optimal growth of the strain expressing the tdcB gene. Further investigations showed that specifically an addition of valine or methionine led to a partial recovery of the growth of this strain, 80 and 86% recovery respectively. The addition of these two amino acids together gave a total growth recovery. Thus the overexpression of the feedback-resistant threonine dehydratase draws carbon away from the valine pathway. The isoleucine and valine pathways compete for pyruvate (FIG. 1) as a substrate. The enzyme AHAS catalyzes the second reaction of the isoleucine pathway by condensing alpha-ketobutyrate and pyruvate and also catalyzes the first reaction of the valine pathway by condensing two molecules of pyruvate. In contrast to *E. coli*, it has been shown that no isoenzymes of AHAS exist in *C. glutamicum* (Eggeling, L., et al., *Appl. Microbiol. Biotechnol.* 25:346–351 (1987)). The same authors showed that this enzyme has a higher $V_{max}$ and a 3-fold higher affinity for alpha-ketobutyrate than for pyruvate. Moreover, the inhibitory effect of alpha-ketobutyrate on the growth of *C. glutamicum* has been already reported (Eggeling, L., et al., *Appl. Microbiol. Biotechnol.* 25:346–351 (1987)). Similarly, this inhibition can be overcome by addition of valine plus leucine. Thus the increase of the catabolic threonine dehydratase leads to an increase of the amount of available alpha-ketobutyrate. This alpha-ketobutyrate then out competes pyruvate leading to more acetohydroxybutyrate synthesis than acetolactate synthesis. The end result is that the valine supply falls short (excess leucine has been supplied in the medium). Similarly, overcoming the growth inhibition of the strain comprising pAPE7 by addition of methionine in the medium could be explained by the fact that the overexpression of the catabolic threonine dehydratase directs carbon flux preferentially from homoserine to threonine at the expense of the methionine pathway leading also to a reduced supply of methionine precursors.

Expression of the tdcB gene under aerobic conditions was accomplished by introducing a heterologous promoter. The regulatory properties of this enzyme were not altered. The catabolic threonine dehydratase in *E. coli* is normally inhibited by high concentrations of pyruvate and some other alpha-keto acids, but this inhibition can be completely overcome by increased levels of AMP (Feldman, D. A. & Datta, P., *Biochem.* 14:1760–1767 (1975)). While these effectors may be operating in Corynebacterium, it is clear that there is sufficient threonine dehydratase activity in the tdcb-carrying strain to promote isoleucine production. As a result, the production of isoleucine has been increased by a factor 50, and 70% of the carbon available for the lysine pathway has been directed into the isoleucine pathway. Expressing this enzyme in strains with different genetic backgrounds, such as, for example, a threonine overproducing strain, would provide an additional benefit in terms of isoleucine production.

Threonine dehydratase (sometimes called "threonine deaminase") is an enzyme that catalyzes the conversion of threonine into alpha-ketobutyrate and ammonia. This enzyme is a critical component in the pathway toward isoleucine biosynthesis and has been the subject of research in the last several years for the purposes of creating isoleucine overproducing strains of bacteria.

In addition to the threonine dehydratases involved in isoleucine biosynthesis, *Escherichia coli* and *Salmonella typhimurium* possess catabolic threonine dehydratases dedicated to the breakdown of threonine in the cell (Bhadra, R. & Datta, P., *Biochem.* 179:1691–1699 (1978)). While these catabolic enzymes also generate alpha-ketobutyrate, it is clear that regulation of their expression and activity is very different from regulation of the biosynthetic forms of the enzymes. Specifically, whereas the "biosynthetic" threonine dehydratases (such as those encoded by the ilvA genes of Corynebacterium and *E. coli*) that are involved in isoleucine biosynthesis are inhibited by high levels of isoleucine, catabolic threonine dehydratases are not inhibited by isoleucine to the same extent and retain more of their activity even as cells accumulate isoleucine.

In addition to the aforementioned capability of producing L-isoleucine, a nonhuman organism of the present invention may have the known characteristics which are effective in enhancing its capability of producing an amino acid, for example, various nutrient requirements, resistance to drugs, sensitivity to drugs, and drug dependence, or characteristics wherein a gene promoting the biosynthesis of an amino acid is amplified by means of gene engineering. Methods of gene amplification in order to increase copy number are known in the art. See, for example, U.S. Pat. Nos. 4,980,285; 5,631,150; 5,707,828; 5,759,828; 5,888,783 and, 5,919,670, and, Sambrook et al., *Molecular Cloning: A Laboratory Manual*, 2nd Ed., Cold Spring Harbor Press (1989).

The method of production of L-isoleucine of the invention can be performed by culturing the nonhuman organism of the present invention in a liquid medium to allow L-isoleucine to be produced. The L-isoleucine thus produced is accumulated in the liquid medium, and collected from this liquid medium. In another embodiment, the L-isoleucine-producing nonhuman organism of the present invention is also used in the production of L-lysine, any other L-amino acid or any amino acid precursor.

In the L-isoleucine producing method of the present invention which is the cultivation of the L-isoleucine-producing nonhuman organism, the collection and purification of L-isoleucine from the culture medium may be performed in a manner similar to the conventional fermentation method wherein an amino acid is produced using a nonhuman organism. A medium used for culture may be either a synthetic medium or a natural medium, so long as the medium includes a carbon source and a nitrogen source and minerals and, if necessary, appropriate amounts of nutrients which the nonhuman organism requires for growth. The carbon source may include various carbohydrates such as glucose and sucrose, and various organic acids. Depending on the mode of assimilation of the used nonhuman organism, alcohol including ethanol, methanol and glycerol may be used. As the nitrogen source, various ammonium salts such as ammonia and ammonium sulfate, other nitrogen compounds such as amines, a natural nitrogen source such as peptone, soybean-hydrolysate and yeast extract are used. Many other sources are known in the art. As minerals, potassium monophosphate, magnesium sulfate, sodium chloride, ferrous sulfate, manganese sulfate, calcium carbonate, etc., are used. Such methods are known in the art. See, for example, U.S. Pat. Nos. 4,980,285; 5,631,150; 5,707,828; 5,759,828; 5,888,783 and, 5,919,670, and, Sambrook et al., *Molecular Cloning: A Laboratory Manual*, 2nd Ed., Cold Spring Harbor Press (1989).

After cultivation, solids such as cells can be removed from the culture medium by gravity, centrifugation and/or membrane filtration, and then the target L-isoleucine can be collected and purified by ion-exchange, ion exclusion, concentration, chromatographic and crystallization methods. The methods of 5 recovery, isolation, purification and crystallization are by any means known to those of skill in the art. Further, L-isoleucine is produced either continuously, or, in batch culture. The culture media containing the synthesized L-isoleucine over-producing nonhuman organism is analyzed at any time before, during or after the culturing for the presence and/or amount of L-isoleucine produced. Methods of collecting and purifying amino acids are known in the art. See, for example, U.S. Pat. Nos. 4,980,285; 5,707,828; 5,759,828; 5,888,783 and, 5,919,670, and, Sambrook et al., *Molecular Cloning: A Laboratory Manual*, 2nd Ed., Cold Spring Harbor Press (1989).

The mechanism for transforming the host cell to direct carbon flow into the divergent pathway preferably involves the insertion of genetic elements including control sequences and sequences coding for catabolic threonine dehydratase. Regardless of the exact mechanism utilized, it is contemplated that the expression of these enzymatic activities will be effected or mediated by the transfer of recombinant genetic elements into the host cell. In a preferred embodiment of the invention, the recombinant genetic element is a transgene wherein the transgene is a catabolic threonine dehydratase gene from *E. coli* or a catabolic threonine dehydratase gene from *Salmonella typhimurium*. It is further envisioned that the catabolic threonine dehydratase gene may be from any prokaryotic or eukaryotic organism. Further, the prokaryotic organism is cryophilic, mesophilic or thermophilic.

The genetic elements of the present invention can be introduced into a nonhuman organism by vectors such as plasmids, cosmids, phages or viral vectors that mediate transfer of the genetic elements into a nonhuman organism. These vectors can include an origin of replication along with cis-acting control elements that control replication of the vectors and the genetic elements carried by the vectors. Selectable markers can be present on the vectors to aid in the identification of nonhuman organisms into which the genetic elements have been introduced. For example, selectable markers can be genes that confer resistance to particular antibiotics such as tetracycline, ampicillin, chloramphenicol, kanamycin, or neomycin. Other selectable markers known in the art are suitable in the practice of the invention. See, for example, U.S. Pat. Nos. 4,980,285;

5,631,150; 5,707,828; 5,759,828; 5,888,783 and, 5,919,670, and, Sambrook et al., *Molecular Cloning: A Laboratory Manual*, 2nd Ed., Cold Spring Harbor Press (1989).

The expression of a gene is primarily directed by its own promoter, although other genetic elements including optional expression control sequences such as repressors and enhancers can be included to control expression or derepression of coding sequences for proteins, apoproteins, or antisense constructs.

In addition, DNA constructs can be generated whereby the gene's natural promoter is replaced with an alternative promoter to increase expression of the gene product. Promoters can be either constitutive or inducible. A constitutive promoter controls transcription of a gene at a constant rate during the life of a cell, whereas an inducible promoter's activity fluctuates as determined by the presence (or absence) of a specific inducer, or in response to developmental or environmental cues. For example, control sequences can be inserted into wild type nonhuman organisms to promote overexpression of selected enzymes already encoded in the genome of the nonhuman organism, or alternatively can be used to control synthesis of extrachromosomally (episomal) encoded enzymes. The nucleic acid construct is introduced into the nonhuman organism by contacting the nonhuman organism with the nucleic acid construct. Types of contacting include transduction, transformation or transfection, or other mechanisms, such as electroporation or microinjection, known to those of skill in the art. See, for example, U.S. Pat. Nos. 4,980,285; 5,631,150; 5,707,828; 5,759,828; 5,888,783 and, 5,919,670, and, Sambrook et al., *Molecular Cloning: A Laboratory Manual*, 2nd Ed., Cold Spring Harbor Press (1989).

Catabolic threonine dehydratases that are much less sensitive to isoleucine inhibition will be useful in any technology that requires a threonine dehydratase to function under conditions where isoleucine may be present in high concentrations, high enough to inhibit all or some of the activity normally carried out by the "biosynthetic" enzyme, or under conditions where other inhibitors are present, such as amino acid analogues. In many biological systems, the native, anabolic threonine dehydratase is sensitive to feedback inhibition by isoleucine or molecules that resemble isoleucine (e.g., synthetic analogs of isoleucine). Thus a drug or other compound may act by inhibiting this enzyme, thereby starving a cell for isoleucine, alpha-ketobutyrate or some other threonine catabolite. Similarly, a herbicide that mimics the effect of isoleucine and inhibits this enzyme would starve the cell, tissue or whole plant of these compounds. Because they are less sensitive to isoleucine-mediated inhibition, catabolic threonine dehydratases such as that encoded by tdcB can be used to produce cells, plants, etc, that are resistant to such drugs or herbicides. Applications of this technology can be envisioned to produce, for example, herbicide resistant crops and drug resistant cell lines. Such applications include prokaryotic, eukaryotic, or in vitro systems where threonine is determined by the enzyme in order to supply metabolites or precursors for other cellular processes or products.

Advances in recombinant DNA technology coupled with advances in plant transformation and regeneration technology have made it possible to introduce new genetic material into plant cells, plants or plant tissue, thus introducing new traits, e.g., phenotypes, that enhance the value of the plant or plant tissue. Thus, there has developed a strong interest in engineering the genome of plants to contain and express foreign genes, or additional, or modifed versions of native, or endogenous genes (perhaps driven by different promoters) in order to alter the traits of a plant in a specific manner. See, for example, U.S. Pat. No. 6,005,168. Demonstrations of the production of herbicide tolerant plants (DeBlock, M. et al., *EMBO J.* 6:2513 (1987)) highlight the potential for crop improvement. The target crops can range from trees and shrubs to ornamental flowers and field crops. "Crop" as used herein can also be a culture of plant tissue grown in a bioreactor as a source for some natural product. See, for, example, U.S. Pat. No. 5,942,662.

Various methods are known in the art to accomplish the genetic transformation of plants and plant tissues using transgenes. See, for example, U.S. Pat. Nos. 5,942,662, 5,990,390 and 6,005,168. These include transformation by Agrobacterium species and transformation by direct gene transfer. Transformation of plant cells mediated by infection with *Agrobacterium tumefaciens* and subsequent transfer of the T-DNA alone have been well documented (Bevan, M. et al., *Int. Rev. Genet.* 16: 357 (1982)). Other gene transfer procedures have been developed to transform plants and plant tissues without the use of an Agrobacterium intermediate (Koziel et al., *Biotechnology* 11: 194–200 (1993)). In the direct transformation of protoplasts the uptake of exogenous genetic material into a protoplast may be enhanced by use of a chemical agent or electric field. The exogenous material may then be integrated into the nuclear genome (Paszkowski, J. et al., *EMBO J.* 3: 2717 (1984) and Potrykus, I. et al., *Mol. Gen. Genet.* 199: 169 (1985)). Polyethylene glycol (PEG)-mediated DNA uptake has been demonstrated in protoplasts (Lorz et al., 1985). DNA may be introduced into intact plant cells by electroporation (PCT WO 92/12250). Alternatively, exogenous DNA can be introduced into cells or protoplasts by microinjection (Reich, T. J. et al., *Bio/Technology* 4: 1001 (1986)). One procedure for direct gene transfer involves bombardment of cells by microprojectiles carrying DNA (Klein, T. M. et al., *Nature* 327:70 (1987)). Other methods may also be used for introduction of DNA into plant cells, for example, by agitation of cells with DNA and silicon carbide fibers.

Techniques for transforming a wide variety of higher plant species are well known and described in the technical and scientific literature. See, for example, Weising et al., *Ann. Rev. Genet.* 22: 421–477 (1988).

Vectors for use in accordance with the present invention may be constructed to include one or more regulatory elements controlling gene expression in plants. Such elements include enhancer elements, promoter elements, transcriptional sequences, translational sequences, termination sequences or any other regulatory element known to those of skill in the art. Examples of enhancer elements useful in the practice of the invention include the ocs enhancer. Many other promoters useful in plant tissue expression are known to those of skill in the art.

Promoters which direct specific or enhanced expression in certain plant tissues are known to those of skill in the art. These include, for example, the rbcS promoter, specific for green tissue; the ocs, nos and mas promoters which have higher activity in roots or wounded leaf tissue; a truncated (−90 to +8) 35S promoter which directs enhanced expression in roots, an alpha-tubulin gene that directs expression in roots and promoters which direct expression in endosperm. Other known promoters include CaMV 35S promoter, CaMV 19S, nos, Adh, sucrose synthase, alpha-tubulin, actin, cab, PEPCase or those associated with the R gene complex. Tissue specific promoters such as root cell promoters and tissue specific enhancers are also contemplated to be particularly useful, as are inducible promoters such as ABA- and turgor-inducible promoters.

Novel promoters or enhancers which are homologous or tissue specific (e.g., root-, collar/sheath-, whorl-, stalk-, earshank-, kernel- or leaf-specific) are envisioned in the practice of the invention. It is also envisioned that one use of the present invention will be the expression of a catabolic threonine dehydratase gene in a tissue-specific manner.

Vectors will also include a 3' end DNA sequence that acts as a signal to terminate transcription and allow for the poly-adenylation of the resultant mRNA. Known 3' elements are those from the nopaline synthase gene of *Agrobacterium tumefasciens*, the terminator for the T7 transcript from the octopine synthase gene of *Agrobacterium tumefasciens*, and the 3' end of the protease inhibitor I or II genes from potato or tomato. Regulatory elements such as Adh intron 1, sucrose synthase intron or TMV omega element, may further be included where desired.

A leader sequence may also be employed in the practice of the invention. Preferred leader sequences are contemplated to include those which include sequences predicted to direct optimum expression of the attached transgene, i.e., to include a preferred consensus leader sequence which may increase or maintain mRNA stability and prevent inappropriate initiation of translation.

Transformed plant cells which are derived by any of the above transformation techniques can be cultured to regenerate a whole plant which possesses the transformed genotype and thus the desired phenotype such as increased isoleucine expression and/or alpha-ketobutyrate synthesis. Such regeneration techniques rely on hormonal manipulation in a tissue culture growth medium, typically relying on a biocide and/or herbicide marker which has been introduced together with the desired nucleotide sequences.

Plant regeneration from cultured protoplasts is described in Evans et al., Protoplasts Isolation and Culture, Handbook of Plant Cell Culture, pp. 124–176, MacMillilan Publishing Company, New York, 1983; and Binding, Regeneration of Plants, Plant Protoplasts, pp. 21–73, CRC Press, Boca Raton, 1985. Regeneration can also be obtained from plant calli, explants, organs, or parts thereof. Such regeneration techniques are described generally in Klee et al., *Ann. Rev. of Plant Phys.* 38: 467–486 (1987). See, U.S. Pat. No. 5,994,662.

Genes that confer resistance to herbicides are well known in the art. For example, several herbicides, such as an imidazalinone or a sulfonylurea, are known to inhibit the growing point or meristem. Exemplary genes conferring resistance to these herbicides encode mutant ALS and AHAS enzymes (Lee et al., *EMBO J.* 7:1241 (1988); Miki et al., *Theor. Appl. Genet.* 80: 449 (1990), and U.S. Pat. No. 5,952,553). Another herbicide, glyphosate, has resistance imparted by mutant 5-enolpyruvyl-3-phosphoshikimate synthase (EPSP) encoded by the aroA gene. U.S. Pat. No. 4,940,835 discloses the nucleotide sequence of a form of EPSP which can confer glyphosate resistance. The nucleotide sequence of the mutant aroA gene is disclosed in U.S. Pat. No. 4,769,061. Nucleotide sequences of glutamine synthetase genes which confer resistance to herbicides such as L-phosphinothricin are disclosed in European patent application No.0333 033, and U.S. Pat. No. 4,975,374. The nucleotide sequence of a phosphinothricin-acetyltransferase gene is provided in European patent application No. 0 242 246. De Greef et al. (*Bio/Technology* 7: 61 (1989)) describe the production of transgenic plants that express chimeric bar genes coding for phosphinothricin acetyl transferase activity. Genes conferring resistance to phenoxy proprionic acids and cyclohexones, such as sethoxydim and haloxyfop, are the Accl-S1, Accl-S2 and Accl-S3 genes, (Marshall et al., *Theor. Appl. Genet.* 83: 435 (1992)). See also U.S. Pat. No. 6,005,168. The deh gene encodes the enzyme dalaphon dehalogenase and confers resistance to the herbicide dalapon. The bxn gene codes for a specific nitrilase enzyme that converts bromoxynil to a non-herbicidal degradation product. Other genes conferring resistance to other herbicides are known in the art. See, for example, U.S. Pat. No. 5,990,390.

The presence of the transgene can be detected by any method known to those of skill in the art. Such methods, include, but are not limited to amplification techniques, such as PCR, for example, and, Southern hybridization techniques and modifications thereof, such as dot or slot hybridization, for example.

In any biological system where breakdown products of threonine are required for useful biological process, the tdcB gene may be used by itself, in place of, or to supplement, existing enzymes because of its insensitivity to feedback regulation. One application of this technology is the production of biopolymers. Metabolism of threonine to alpha-ketobutyrate is an important step in synthesizing useful precursors for biopolymer synthesis. Catabolic threonine dehydratase converts threonine to alpha-ketobutyrate. The alpha-ketobutyrate is metabolized further, for example to useful CoenzymeA derivatives such as propionyl-CoA, and the subsequent metabolites can be incorporated into polymers such as polyhydroxyalkanoates (PHAs). This strategy is especially useful for producing co-polymers such as poly-(hydroxybutyrate-co-hydroxyvalerate) (PHBVs). If a cell has only a "normal" feedback sensitive, anabolic threonine dehydratase, it typically cannot synthesize enough of the alpha-ketobutyrate to supply the needs of polymer synthesis. Applications of this technology can be easily envisioned for use in both prokaryotic systems (e.g. bacterial) and eukaryotic systems (e.g. plants and fungi). See, for example, U.S. Pat. Nos. 5,958,745; 5,534,432; 5,245,023; 5,480,794; 5,334,520; 5,518,907; 5,344,769; 5,135,859; 5,602,321; 5,663,063; 5,250,430 and 5,942,660. See, also, Valentin, H. E., et al., *Int. J. Biol. Macromol.* 25(1–3): 303–306 (1999).

The present invention is described in further detail in the following non-limiting examples.

EXAMPLES

The following protocols and experimental details are referenced in the examples that follow.

I. Strains, Plasmids and Media

Bacterial strains and plasmids are listed in Table 1. LB medium or 2xYT medium (Sambrook, J., et al., *Molecular Clonning: A Laboratory Manual*, 2nd ed., Cold Spring Harbor Laboratory, Cold Spring Harbor, N.Y. (1989)) was used as a standard medium, and a medium containing 40 g·l$^{-1}$ brain-heart infusion, 20 g·l$^{-1}$ sorbitol and 10 g·l$^{-1}$ sucrose was used as a recovery broth for electroporated cells. Minimal medium for *E. coli* was M9 medium. *E. coli* AB1255 (Pittard, J. & Adelberg, E. A., *J. Bacteriol.* 85:1402–1408 (1963)) was obtained from the *E. coli* Genetic Stock Center, Department of Biology, Yale University, New Haven, Conn. 06520, courtesy of Barbara Bachman, and minimal medium for this strain was supplemented with 100 mg·l$^{-1}$ each of histidine, arginine, and methionine.

Defined medium for *Corynebacterium glutamicum* contained the following ingredients (per liter): glucose, 35 g; NaCl, 2 g; citrate (trisodium salt, dihydrate), 3 g;

CaCl$_2$.2H$_2$O, 0.1 g; MgSO$_4$.7H$_2$O, 0.5 g; Na$_2$EDTA.2H$_2$O, 75 mg; FeSO$_4$.7H$_2$O, 50 mg; 100×salt solution, 20 ml; K$_2$HPO$_4$, 4 g; KH$_2$PO$_4$, 2 g; (NH$_4$)$_2$SO$_4$, 7.5 g; urea, 3.75 g; leucine 0.85 g; thiamine, 0.45 mg; biotin, 0.45 mg; pantothenic acid, 4.5 mg (pH 7.0). The salt solution contained the following ingredients (per liter): MnSO$_4$, 200 mg; Na$_2$B$_4$O$_7$.10H2O, 20 mg; (NH$_4$)$_6$Mo$_7$O$_{24}$.4H$_2$O, 10 mg; FeCl$_3$.6H$_2$O, 200 mg; ZnSO$_4$.7H$_2$O CuCl$_2$.2H$_2$O, 20 mg (pH 2.0). When appropriate, kanamycin (150 mg/liter) and isopropyl-β-D-thiogalactopyranoside (IPTG) (150 mg/l) was used.

For the growth study with amino acid supplements, the defined medium was complemented with Bacto® casamino acids (Difco, Detroit, Mich.) at a concentration of 2 g·l$^{-1}$ or with amino acid (alanine, glycine, methionine or valine) at a concentration of 0.5 g·l$^{-1}$ each.

TABLE 1

Bacterial strains. AEC$^R$ denotes resistance to aminoethylcysteine

| Strains | Genotype or Description | Source or Reference |
| --- | --- | --- |
| C. glutamicum AS019-E12 | restriction deficient derivative of C. glutamicum AS019 | Follettie. M.T., et al., Mol. Microbiol. 2:53–62 (1988) |
| C. glutamicum ATCC21799 | Lysine-producing strain, Leu$^-$. AEC$^R$, Pan | ATCC |
| E.coli BW310 | λ$^-$, ung-I, relA1, spoT1, thi-1 | Duncan, B.K & Weiss, B., J. Bacteriol. 151:750–755 (1982) |
| AB1255 | ilvA201 metB1 hisG1 argH1 | Pittard, J., and Adelberg, E.A., J. Bacteriol. 85:1402–1408 (1963) |

Figure 2:
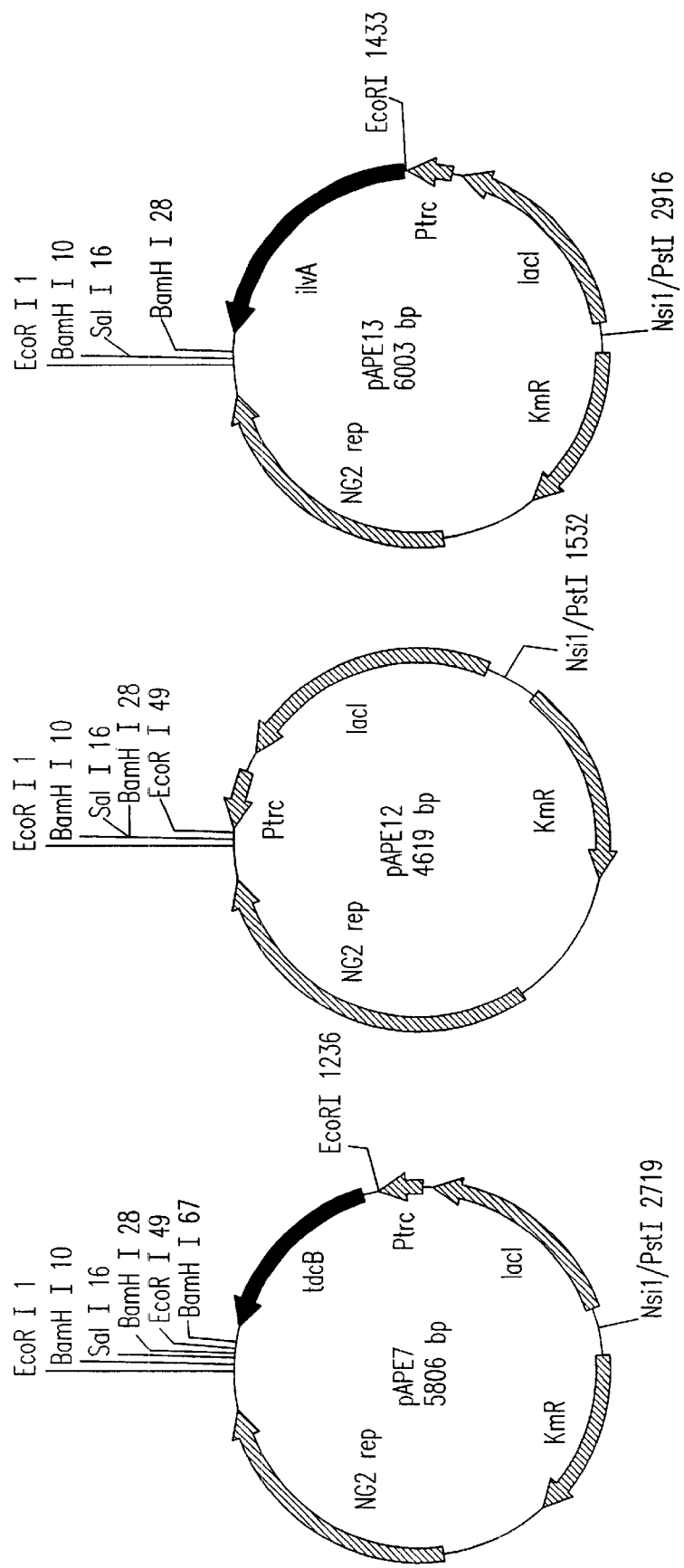
FIG. 2. Plasmid maps. NG2 rep, ORF from the NG2 replicon permitting plasmid replication in both *E. coli* and *C. glutamicum*; $P_{trc}$, trc promoter from pTrc99a; lacI, ORF encoding lac repressor from pTrc99a; $Km^R$, kanamycin resistance gene from pEP2; NsiI/PstI denotes position of hybrid NsiI and PstI sites resulting from ligation.

II. Cloning tdcB and ilvA coding regions were amplified by the Polymerase Chain Reaction (PCR) (Table 2), from BW310 genomic DNA and from pGC77 (Km$^R$, Ap$^R$, LacI$^q$, hom$^{dr}$, tac::thrB, ilvA)(Table 1), respectively. The PCR products were cloned into the pCRScript system (Ap$^R$)(Stratagene, La Jolla) creating tdcB-pCRscript (Ap$^R$, tdcB (no promoter)) and pAPE16 (Ap$^R$, irc:ilvA), again respectively. The EcoRI-BamHI fragment of these pCRscript derivatives were cloned into pTrc99a (Ap$^R$, LacI$^q$ trc)(Pharmacia, Upsalla, Sweden) to create pAPE5 (Ap$^R$, LacI$^q$, trc:tdcB) and pAPE17 (Ap$^R$, LacI$^q$, trc:ilvA), respectively. Subsequently, the NsiI-SalI fragments of pAPES (Ap$^R$, LacI$^q$, trc:tdcB), pAPE17 (Ap$^R$, LacI$^q$, trc:ilvA), and pTrc99a (Ap$^R$, including the lacI$^q$ and P$_{trc}$ element) were subcloned into pEP2 (Km$^R$ NG2 rep) (Zhang, Y., et al., J Bacteriol. 176:5718–5728 (1994)), which had been cut with PstI and with SalI, to create pAPE7 (Km$^R$, LacI$^q$, trc:tdcB), pAPE13 (Km$^R$, LacI$^q$, trc:ilvA), and pAPE12 (Km$^R$, LacI$^q$, trc), all of which could replicate both in Corynebacterium and in E.coli, and which expressed the appropriate gene product (or empty control) under control of the trc promoter. Plasmid maps are shown in FIG. 2.

TABLE 2

PCR products and primers

| PCR Product | Template | Description | Primer 1 | Primer 2 |
| --- | --- | --- | --- | --- |
| tdcB | BW310 genomic DNA | Coding region for catabolic threonine dehydratase from E.coli | 5'gggaattcggtgtcgg ttacggttacct3' SEQ ID NO: 1 | 5'ccggtaccccaaac aagcctaacgtcca 3' SEQ ID NO: 2 |
| ilvA | pGC77 | Coding region for anabolic threonine dehydratase from C. glutamicum | 5'ggaattcatgagtgaa acatacgtgtctga 3' SEQ ID NO: 3 | 5'ccacgcgtggggctt tgcgatcct 3' SEQ ID NO: 4 |

III. Enzyme Assays

Enzyme assays were performed with cell free crude extracts, prepared by the following method. Cells were harvested by centrifugation for 10 min at 5000×g at 4° C. and washed with 10 ml of the enzyme assay buffer (100 mM Tris-HCl, pH 7.5, containing 20 mM KCl, 5 mM MnSO$_4$, 0.1 mM EDTA, and 2 mM dithiothreitol) (Jetten, M. S. M., et al., Appl. Microbiol. Biotechnol. 41:47–52 (1994)). The cell pellet was resuspended in the same buffer containing a protease inhibitor cocktail (Boehringer Mannheim, Germany) so that the final concentration was 20 g dry cell weight·l$^{-1}$. Resuspended cells were disrupted with a glass bead mixer (5100 Mixer-Mill, SPEX, Metuchen, N.J.). 2.5 ml of bacterial suspension was poured in a frozen steel vial containing 5 g of cold 106 vm-diameter glass beads (Sigma) and one stainless steel ball bearing. The vials containing bacterial suspension and glass beads were vigorously shaken at 4° C. using the mixer by 10 cycles of 30 sec shaking separated by rest cycles of one minute. Cell debris were removed by centrifugation for 20 min at 47000×g at 4° C. The supernatant (crude extract) was then tested for enzyme activity. Protein concentrations were determined by the method of Bradford (Bradford, M. M., Anal. Biochem. 72:248–254 (1976)) with the Bio-Rad (Hercules, Calif.) protein assay kit using bovine serum albumin as a standard.

For determination of threonine dehydratase activity, the assay mixture contained 40 mM threonine, 1 mM pyridoxal phosphate, crude extract and 100 mM potassium phosphate buffer, pH 8.0 in a final volume of 1 ml. The reaction was started with the addition of threonine and terminated by the addition of 1 ml solution containing 1% semicarbazide and 0.9% sodium acetate. After a 15 min incubation at room temperature, the amount of alpha-ketobutyrate formed at various intervals was measured spectrophotometrically as its semicarbazone derivative at 254 nm (=0.52 mmol·cm$^{-1}$). Relevant standards and controls were carried out in the same manner. For specific determination of catabolic threonine dehydratase activity, the assay mixture contained 20 mM isoleucine in order to inhibit the anabolic threonine dehydratase.

In FIGS. 3–6, the results of the enzymatic assays are expressed in terms of relative expression of threonine dehydratase compared to wild type expression as the ratio between the specific activity of the enzyme of a strain and the specific activity of the wild type. Each assay was replicated five times, and the results were reproducible within 15%.

IV. Fermentations

Starter cultures of *Corynebacterium glutamicum* were prepared by transferring one colony from LB agar plates to 5 ml of LB medium. These cultures were incubated for two days at 30° C. and 200 rpm. 500 ml-Erlenmeyer flasks containing 50 ml of defined medium were inoculated with 1 ml of the starter culture. Cultures were incubated at 30° C. and 200 rpm for 30 hours. These flask cultures were used as a 5% (v/v) inoculum for 2 liters of defined medium in a 4-liter Chemap CMF100 reactor (Alfa-Laval Chemap, Switzerland). The culture was grown at 30° C. with an aeration rate of 0.45 VVM and an agitation rate of 1500 rpm. The pH was maintained at 7.5 with ammonium hydroxide and hydrochloric acid solutions. Fermentations were carried out twice for each strain.

V. Determination of Biomass, Sugars, Organic Acids and Amino Acids

During the fermentation, samples were collected and centrifuged at 10,000×g, 4° C., for 10 minutes. For biomass determination, cell dry weight was determined gravimetrically.

For determination of glucose, organic acids and amino acids, samples were collected and filtered through 0.2 μm Acrodisc® filters (Gelman Sciences, Ann Arbor, USA). Sugars and organic acid concentrations were determined by HPLC (Hewlett Packard model 1050, Waldbronn, Germany) using an Aminex® HPX-87H column (Bio-Rad, Hercules, USA). Sample analysis was performed at 40° C. using 5 mM sulfuric acid as the mobile phase at a flow rate of 0.6 ml·min$^{-1}$. The detection of sugars was performed with a refractive index detector (Hewlett Packard model 1047A) and the detection of organic acids with a UV detector (Hewlett Packard model 1050). Results from replicate measurements of glucose were reproducible within 5%.

Amino acids were analyzed as ortho-phthaldialdehyde derivatives by reversed-phase chromatography using a C 18 AminoQuant column with a Hewlett Packard series 1050 high-pressure liquid chromatography (HPLC) system (Hewlett Packard, Waldbronn, Germany). Amino acid determinations were reproducible within 5% in replicate assays.

Example 1

Overexpression of tdcB in *E. coli* and in *C. glutamicum*

Enzyme assays for threonine dehydratase activity were conducted on crude extracts from an *E. Coli* strain (AB1255) which cannot produce anabolic threonine dehydratase (encoded by the ilvA gene) and the same strain carrying the pAPE5 plasmid containing the tdcB gene. Even in the presence of very high concentrations of isoleucine (up to 47 mM), the AB1255 (pAPE5) extracts showed consistent activity at about 80 μmol product·min$^{-1}$·mg protein$^{-1}$, while AB1255 (pTrc99a) control extracts had no measurable activity at any isoleucine concentration. These results indicate that the tdcB gene product can be overexpressed in aerobic conditions in *E. coli* while still retaining function.

In order to test expression of the catabolic threonine dehydratase in Corynebacterium, the trc:tdcB fusion was subcloned from pAPE5 into the expression vector pAPE12, and this plasmid (pAPE7) was expressed in *C. glutamicum* AS019-E12. Whereas a control strain of *C. glutamicum* AS019-E12 carrying pAPE12 had no detectable catabolic threonine dehydratase activity, the strain carrying pAPE7 produced 9 μmol product·min$^{-1}$·mg protein$^{-1}$. Although the activity measured in crude extracts of this strain was about 10-fold lower than that in *E. coli*, the activities are actually proportional to the differences in plasmid copy number in these two bacteria, in that pAPE7 is expected to have a 10-fold lower copy number in Corynebacterium than pAPE5 has in *E. coli*. These results show that tdcB is expressed in the heterologous species.

Cultures of *Corynebacterium glutamicum* ATCC 21799 comprising plasmid pAPE13(ilvA) and *Corynebacterium glutamicum* ATCC 21799 comprising plasmid pAPE7 (tdcB) were deposited under the terms of the Budapest Treaty on the International Recognition of the Deposit of Nonhuman organisms for Purposes of Patent Procedure at the American Type Culture Collection (ATCC), 10801 University Boulevard, Manassas, Va. 20110–2209. The deposits of the cultures of the mutants were accepted by that Depositary under the terms of that Treaty. The deposit of *Corynebacterium glutamicum* ATCC 21799 comprising plasmid pAPE7 (tdcB) was assigned deposit number PTA-98 1. The deposit of *Corynebacterium glutamicum* ATCC 21799 comprising plasmid pAPE12(Km$^R$, LacI$^q$, trc) was assigned deposit number PTA-979. The deposit of *Corynebacterium glutamicum* ATCC 21799 comprising plasmid pAPE13 (ilvA) was assigned deposit number PTA-980. The deposit of *Corynebacterium glutamicum* ATCC 21799 comprising plasmid pAPE18 (tdcB, hom$^{dr}$, Ptrc, thrB, Ptac, Km$^R$, rep) was assigned deposit number PTA-978.

Example 2

Isoleucine Sensitivity of the Threonine Dehydratases

Figure 3:
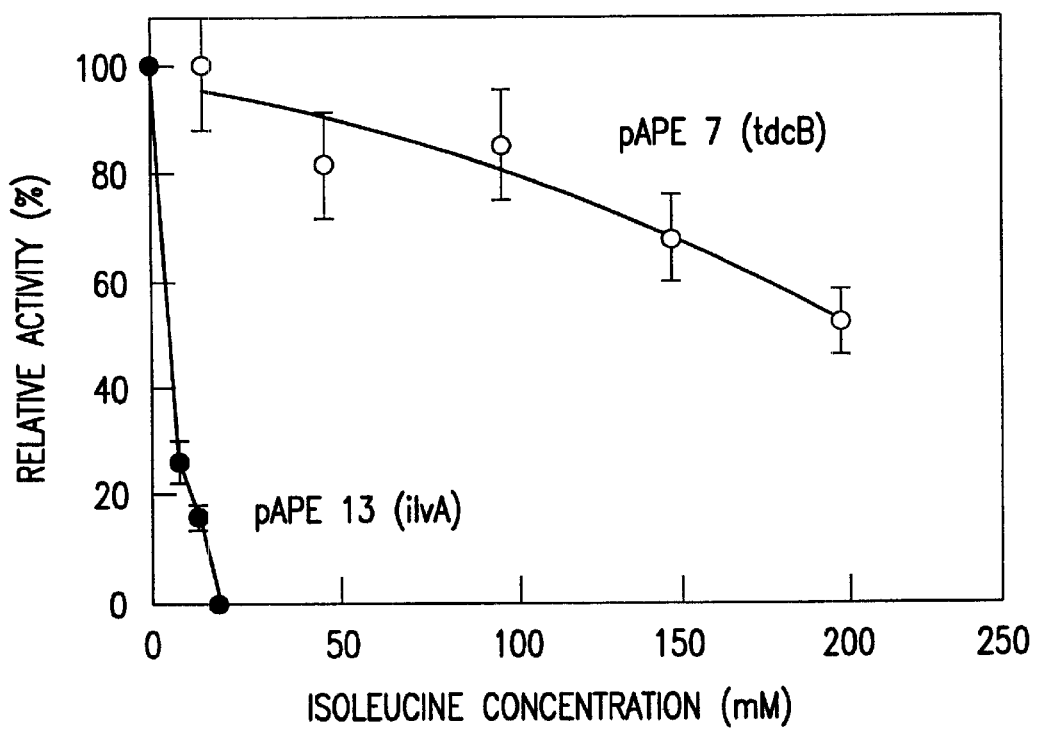
FIG. 3. Sensitivity of threonine dehydratases expressed in Coryne-bacterium glutamicum ATCC 21799 to varying isoleucine concentrations.
Figure 4A:
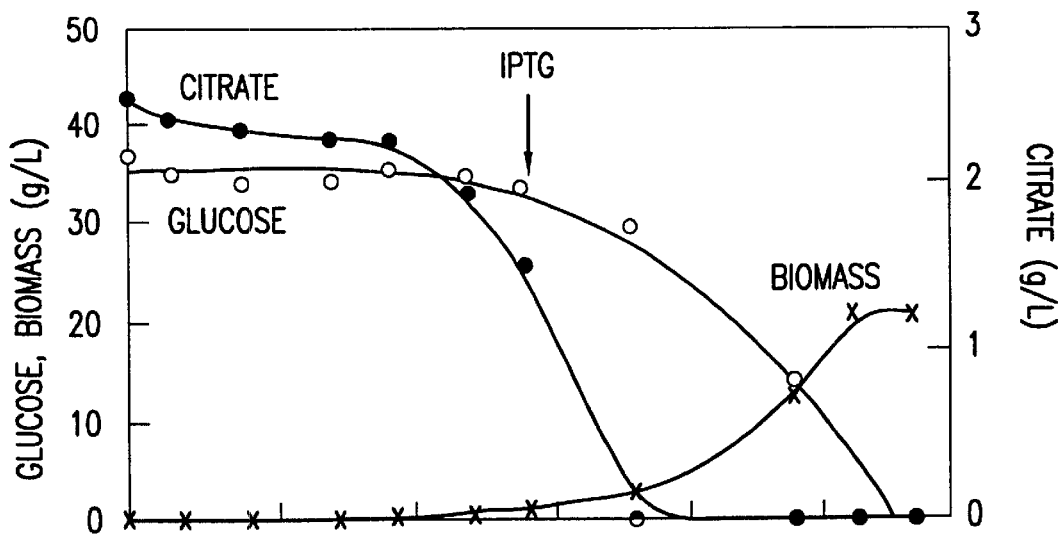
FIGS. 4A, 4B. Culture of *C. glutamicum* ATCC 21799 in batch reactor on defined medium. Kinetics of growth, substrate consumption (A), and amino acid production (B). IPTG, arrow indicates point at which IPTG was added to the culture. In this culture, addition of IPTG did not lead to an increase in threonine dehydratase (not shown).
Figure 4B:
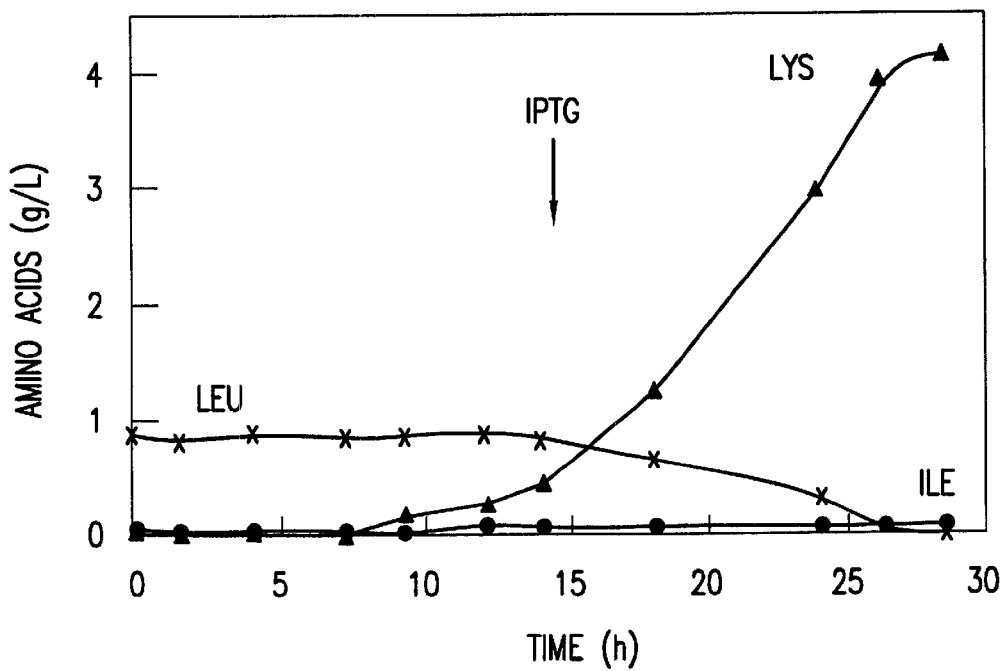

In order to confirm the insensitivity to isoleucine of catabolic dehydratase expressed in a lysine producing strain of *C. glutamicum*, threonine dehydratase activities were measured in crude extracts of strains ATCC21799 and ATCC21799 carrying pAPE7 at different concentrations of isoleucine (FIG. 3). Anabolic threonine dehydratase of the wild type strain ATCC21799 was totally inhibited by an isoleucine concentration of 15 mM. On the other hand, catabolic threonine dehydratase expressed in strain ATCC 21799 (pAPE7) was much less sensitive to isoleucine. It retained 60% of its original activity even at a concentration of 200 mM isoleucine.

Example 3

Fermentation Results

In order to determine whether or not there was an advantage to using the catabolic threonine dehydratase for the production of isoleucine, fermentations were performed with *Corynebacterium glutamicum* ATCC 21799 as a control, and two derivatives of this strain carrying either the pAPE13 plasmid comprising the trc:ilvA fusion or carrying the pAPE7 plasmid comprising the trc:tdcB fusion.

I. Fermentation with the Wild Type Strain

*C. glutamicum* ATCC 21799 was grown twice in defined medium in a 4-liter reactor. IPTG (150 mg/l) was added when the biomass reached 1.5 g cell dry weight·l$^{-1}$. Kinetics of growth, substrate consumption, threonine dehydratase specific activity and amino acid production are shown FIG. 4. This strain grew exponentially with a specific growth rate of 0.3 h$^{-1}$ and a glucose to biomass conversion yield of 0.53 g cell dry weight·g glucose$^{-1}$. The basal level of threonine dehydratase stayed constant around 1 μmol alpha-ketobutyrate·min$^{-1}$·mg protein$^{-1}$ during the fermentation course. The strain produced mainly lysine at final concentrations of 3.9 and 4.2 g·l$^{-1}$, in the two fermentations. A concentration of isoleucine of 50 mg·l$^{-1}$ was detected at the end of both cultures. Oxygenation of the cultures being sufficient, neither lactate nor acetate was detected during the fermentation.

II. Fermentation with the ilvA Overexpressing Strain

Figure 5A:
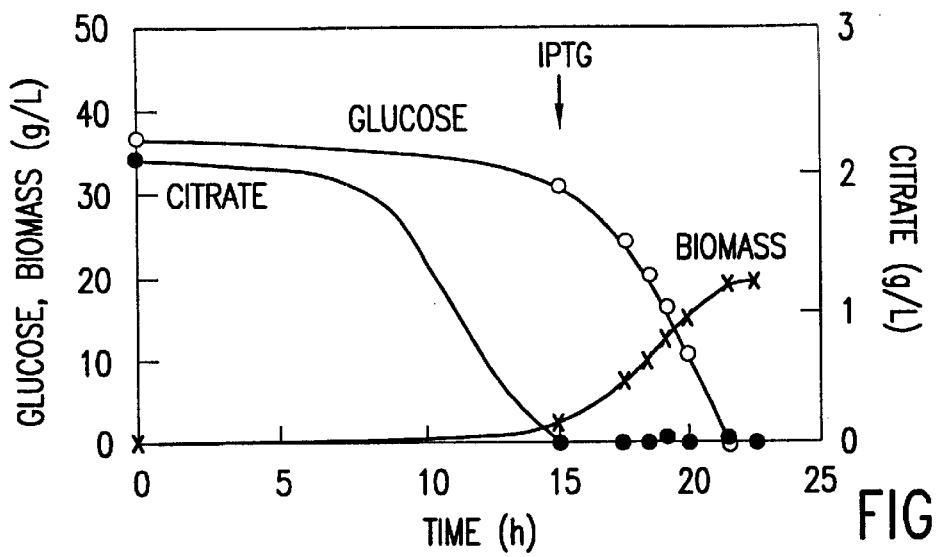
FIGS. 5A, 5B, 5C. Culture of *C. glutamicum* ATCC 21799 (pAPE13) in batch reactor on defined medium. Kinetics of growth, substrate consumption (5A), amino acid production (5C) and production of threonine dehydratase (5B). IPTG, arrow indicates point at which IPTG was added to the culture medium.
Figure 5B:
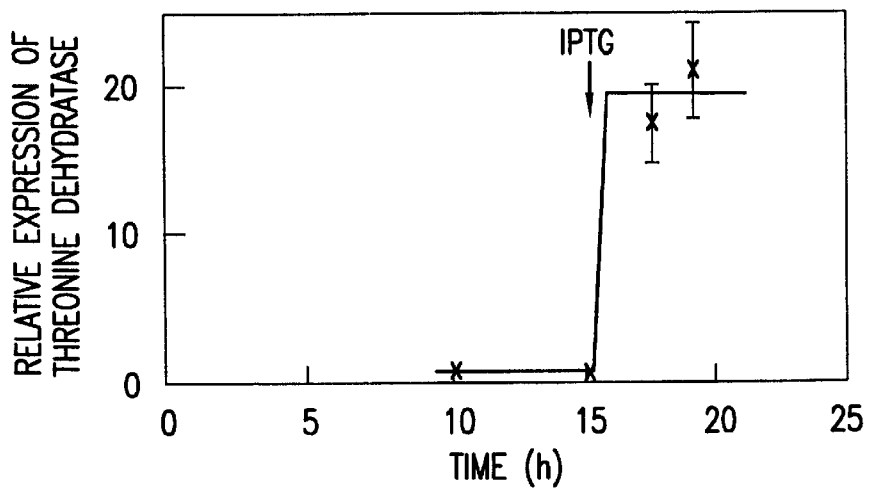
Figure 5C:
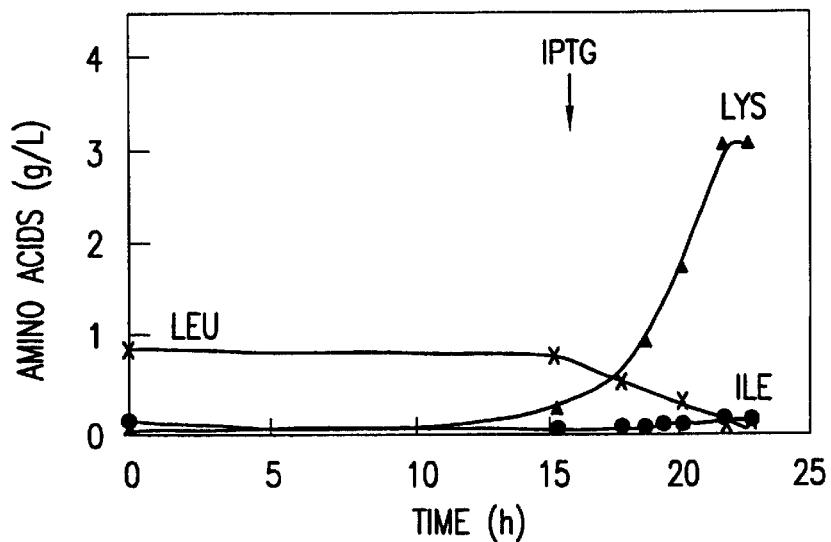

*C. Glutamicum* ATCC 21799 harboring pAPE13 was grown twice in defined medium in a 4 liter reactor. As before, IPTG (150 mg/l) was added when biomass reached 1.5 g cell dry weight·l$^{-1}$(FIG. 5). The specific growth rate and the glucose to biomass conversion yield of this strain were identical to the wild type strain. The addition of IPTG resulted in a 20-fold increase in the level of threonine dehydratase. ATCC 21799 (pAPE13) still produced mainly lysine at final concentrations of 3.2 and 2.9 g·l$^{-1}$ in the two fermentations. The concentration of isoleucine reached a value of 0.2 g·l$^{-1}$ at the end of both fermentations.

III. Fermentation with the tdcB Overexpressing Strain

Figure 6A:
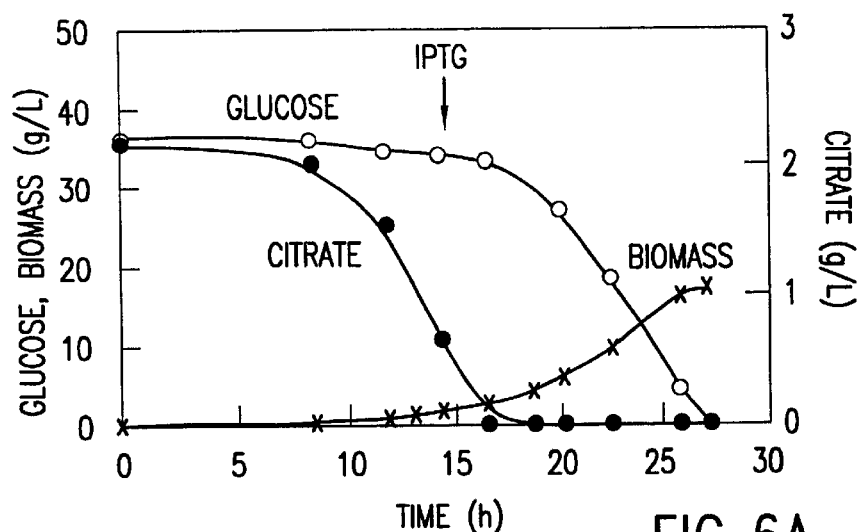
FIGS. 6A, 6B, 6C. Culture of *C. glutamicum* ATCC 21799 (pAPE7) in batch reactor on defined medium. Kinetics of growth, substrate consumption (6A), amino acid production (6C) and production of catabolic threonine dehydratase (6B). IPTG, point at which IPTG was added to the culture medium.
Figure 6B:
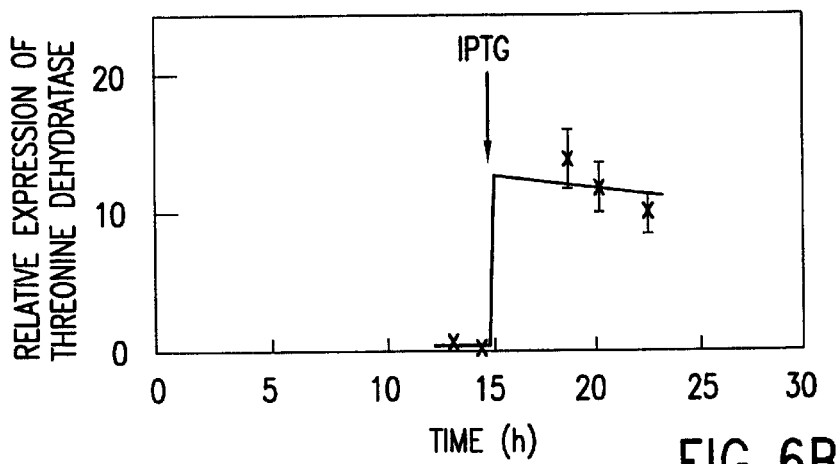
Figure 6C:
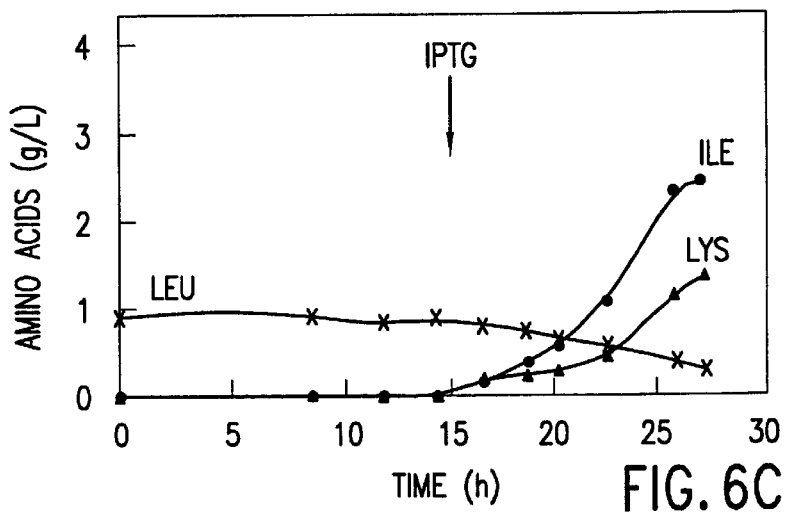

*C. glutamicum* ATCC 21799 harboring pAPE7 was grown twice in defined medium in a 4 liter reactor under the same conditions of agitation, aeration and IPTG addition as the two former strains (FIG. 6). The specific growth rate (0.22 h$^{-1}$) and the glucose to biomass conversion yield (0.46 g.g$^{-1}$) of this strain were lower than those obtained with the wild type strain and ilvA4 overexpressing strain. The addition of IPTG resulted in the synthesis of catabolic threonine dehydratase which reached a 15-fold higher concentration than that of the original enzyme. Catabolic threonine dehydratase activity remained high during the course of the fermentation. As a result, ATCC 21799 (pAPE7) produced 2.5 g·l$^{-1}$ isoleucine and 1.3 g·l$^{-1}$ lysine in the first fermentation, 2.3 g·l$^{-1}$ isoleucine and 1.3 g·l$^{-1}$ lysine in the second fermentation.

Example 4

Growth Study with Amino Acid Supplements

To investigate the slow growth of the tdcB expressing strain, *C. glutamicum* ATCC 21799 containing pAPE7 and pAPE13 were cultured in conical flasks with defined medium supplemented with amino acids (Table 3). The tdcB expressing strain, when cultured on the defined medium supplemented with a mixture of amino acids from a casein hydrolysate (casamino acids), recovered to an optimal growth from 0.17 he without casamino acids to 0.29 h$^{-1}$ with casamino acids. This rate was comparable to the growth of the wild type and ilvA overexpressing strains (0.30 h$^{-1}$). In order to determine which specific amino acid was limiting, causing the slow growth rate in the tdcB expressing strain, the defined medium was supplemented with specific amino acids depending on their potential interaction with the isoleucine pathway. Valine and methionine were chosen to test due to their direct connection with the isoleucine pathway, and alanine and glycine for their indirect connection through the use of pyruvate, which is also a substrate for the isoleucine pathway.

TABLE 3

Growth study of ilvA and tdcB expressing *C. glutamicum* strains on defined medium supplemented with amino acids and containing 150 mg/l IPTG

| | Specific growth rate (h$^{-1}$) | |
| --- | --- | --- |
| Defined medium supplemented with | ATCC 21799 pAPE13ilvA | ATCC 21799 pAPE7tdcB |
| — | 0.30 | 0.17 |
| casamino acids | 0.30 | 0.29 |
| Valine | nd$^a$ | 0.24 |
| Methionine | nd$^a$ | 0.26 |
| Alanine | nd$^a$ | 0.17 |
| Glycine | nd$^a$ | 0.17 |
| Valine + Methionine | nd$^a$ | 0.29 |

($^a$Not Determined)

Results showed that the addition of valine or methionine led to an increase of the specific growth rate (to 0.24 and 0.26 h$^{-1}$, respectively). The addition of both valine and methionine to the defined medium resulted in a growth rate comparable to that seen when casamino acids were added to the medium (0.29 h$^{-1}$). Alanine or glycine alone were unable to restore growth rate (0.17 h$^{-1}$) of the tdcB expressing strain.

Having now fully described the present invention in some detail by way of illustration and example for purposes of clarity of understanding, it will be obvious to one of ordinary skill in the art that same can be performed by modifying or changing the invention with a wide and equivalent range of conditions, formulations and other parameters thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing L-isoleucine comprising:
   (a) growing a transformed nonhuman organism under conditions that provide for synthesis of L-isoleucine, wherein said nonhuman organism comprises one or more copies of a transgene comprising at least one nucleotide sequence of a tdcB gene encoding catabolic threonine dehydratase (E.C.4.2.1.19);
      wherein said L-isoleucine is synthesized by said transformed nonhuman organism, said synthesis being greater than that of a corresponding non-transformed nonhuman organism; and
   (b) recovering said L-isoleucine from said culture media in which said transformed nonhuman organism was cultured.

2. The method of claim 1, wherein said transformed nonhuman organism additionally over-produces one or more of L-lysine, L-methionine, L-leucine, L-valine, L-threonine, L-aspartic acid, and homoserine, wherein said production is greater than that of a corresponding, nontransformed nonhuman organism.

3. The method of claim 1, wherein the transformed nonhuman organism is of the genus Corynebacterium.

4. The method of claim 1, wherein the transformed nonhuman organism is of the genus Escherichia.

5. The method of claim 1, wherein said transgene comprises a tdcB gene from *E. coli*.

6. The method of claim 1, wherein said transgene comprises a catabolic threonine dehydratase gene from *Salmonella typhimurium*.

7. The method of claim 1, wherein said nonhuman organism is transformed with pAPE7.

8. The method of claim 1, wherein said nonhuman organism is *Corynebacterium glutamicum* and said transgene comprises a tdcB gene from *E. coli*.

9. The method of claim 1, wherein said conditions that provide for synthesis of L-isoleucine comprise supplementation of said culture media with one or more amino acids or amino acid precursors.

10. The method of claim 1 for producing L-isoleucine, wherein said nonhuman organism additionally comprises one or more transgenes comprising at least one nucleotide sequence encoding one or more enzymes involved in L-isoleucine biosynthesis.

11. The method of claim 3, wherein said nonhuman organism is *Corynebacterium glutamicum*.

12. The method of claim 4, wherein the transformed nonhuman organism is *Escherichia coli*.

13. The method of claim 9, wherein said one or more amino acids or amino acid precursors is one or more of L-methionine, L-leucine, L-valine, L-threonine, L-lysine, L-aspartic acid, glycine, L-alanine and homoserine.

14. The method of claim 11, wherein said *Corynebacterium glutamicum* is ATCC 21799.

15. The transformed nonhuman organism of claim 10, wherein said one or more enzymes involved in L-isoleucine biosynthesis is one or more of homoserine dehydrogenase, homoserine kinase, acetohydroxy acid synthase, aspartokinase, aspartate β-semialdehyde dehydrogenase, threonine synthase, acetohydroxy acid isomeroreductase, dihydroxy acid dehydratase, and feedback insensitive forms thereof.

16. A method for producing L-isoleucine comprising:
   (a) growing an L-isoleucine producing nonhuman organism comprising one or more copies of a transgene comprising at least one nucleotide sequence of a tdcB gene encoding catabolic threonine dehydratase (E.C.4.2.1.19)
   wherein said non human organism synthesizes L-isoleucine, said synthesis being greater than that of a corresponding nonhuman organism which does not comprise one or more copies of a transgene comprising at least one nucleotide sequence encoding catabolic threonine dehydratase; and (b) recovering said L-isoleucine from said culture media in which said L-isoleucine producing nonhuman organism was grown.

17. The method of claim 16 wherein said nonhuman organism has been genetically manipulated to overproduce one or more of L-lysine, L-methionine, L-leucine, L-valine, L-threonine, L-aspartic acid, and homoserine prior to the introduction of said nucleotide sequence encoding catabolic threonine dehydratase into said nonhuman organism.

18. The method of claim 17 wherein said nonhuman organism comprises hom$^{dr}$ and thrB and overproduces threonine.

19. An L-isoleucine producing nonhuman organism comprising one or more copies of a transgene comprising at least one nucleotide sequence of a tdcB gene encoding catabolic threonine dehydratase (E.C.4.2.1.19), wherein said nonhuman organism synthesizes L-isoleucine, said synthesis being greater than that of a corresponding non-transformed nonhuman organism.

20. The nonhuman organism of claim 19, wherein said nonhuman organism over-produces one or more of L-lysine, L-methionine, L-leucine, L-valine, L-threonine, L-aspartic acid, and homoserine prior to the introduction of said one or more copies of said transgene.

21. The nonhuman organism of claim 19, wherein said nonhuman organism additionally over-produces one or more of L-lysine, L-methionine, L-leucine, L-valine, L-threonine, L-aspartic acid, and homoserine.

22. The nonhuman organism of claim 19, wherein said transgene comprises a catabolic threonine dehydratase gene from *E. coli* or from *Salmonella typhimurium*.

23. The nonhuman organism of claim 19, wherein said transgene comprises a tdcB gene encoding catabolic threonine dehydratase (E.C. 4.2.1.19).

24. The nonhuman organism of claim 19, wherein said nonhuman organism is of the genus Corynebacterium.

25. The nonhuman organism of claim 19, wherein said nonhuman organism is of the genus Escherichia.

26. The transformed nonhuman organism of claim 19, wherein said transformed nonhuman organism additionally comprises one or more transgenes comprising at least one nucleotide sequence encoding one or more enzymes involved in L-isoleucine biosynthesis.

27. The nonhuman organism of claim 24, wherein said nonhuman organism is *Corynebacterium glutamicum*.

28. The nonhuman organism of claim 25, wherein said nonhuman organism is *Escherichia coli*.

29. The transformed nonhuman organism of claim 26, wherein said one or more enzymes involved in L-isoleucine biosynthesis is one or more of homoserine dehydrogenase, homoserine kinase, acetohydroxy acid synthase, aspartokinase, aspartate β-semialdehyde dehydrogenase, threonine synthase, acetohydroxy acid isomeroreductase, dihydroxy acid dehydratase, and feedback insensitive forms thereof.

30. The nonhuman organism of claim 27, wherein said *Corynebacterium glutamicum* is ATCC 21799.

31. An L-isoleucine producing nonhuman organism comprising one or more copies of a transgene comprising at least one nucleotide sequence of a tdcB gene encoding catabolic threonine dehydratase (E.C.4.2.1.19), wherein said nonhuman organism synthesizes L-isoleucine, said synthesis being greater than that of a corresponding nonhuman organism which does not comprise one or more copies of a transgene comprising at least one nucleotide sequence encoding catabolic threonine dehydratase.

32. The nonhuman organism of claim 31 wherein said nonhuman organism has been genetically manipulated to overproduce one or more of L-lysine, L-methionine, L-leucine, L-valine, L-threonine, L-aspartic acid, and homoserine prior to the introduction of said nucleotide sequence encoding catabolic threonine dehydratase into said nonhuman organism.

33. The nonhuman organism of claim 32 wherein said nonhuman organism comprises hom$^{dr}$ and thrB and overproduces threonine.

34. *Corynebacterium glutamicum* ATCC21799 comprising pAPE7, ATCC deposit no. PTA-981.

35. *Corynebacterium glutamicum* ATCC21799 comprising pAPE18, ATCC deposit no. PTA-978.

36. A plant, or plant part thereof, comprising one or more copies of a transgene comprising at least one nucleotide sequence of a tdcB gene encoding catabolic threonine dehydratase, wherein said plant or plant part thereof retains more catabolic threonine dehydratase enzyme activity after contacting herbicide than a corresponding plant, or plant part thereof, contacted with said herbicide, which does not comprise one or more copies of a transgene comprising at least one nucleotide sequence encoding catabolic threonine dehydratase.

37. The plant, or plant part thereof, of claim 36, wherein said plant part is selected from leaves, roots, stems, flowers and flower parts, seeds, pollen, cells and calli.

38. The plant, or plant part thereof, of claim 36 wherein said herbicide comprises an L-isoleucine analog.

39. The plant, or plant part thereof, of claim 36 wherein said plant, or plant part thereof, produces alpha-ketobutyrate and/or isoleucine before contact with, in the presence of, and after said contact with said herbicide.

40. A method of increasing plant growth comprising:
   cultivating the plant, or plant part thereof, of claim 36 in the presence of an herbicide, wherein growth of said plant, or said plant part thereof, is greater than the growth of a corresponding plant, or plant part thereof, contacted with said herbicide, which does not comprise one or more copies of a transgene comprising at least one nucleotide sequence encoding catabolic threonine dehydratase.

41. A method of enhancing resistance to a herbicide in a plant, or plant part thereof, said method comprising introducing into said plant, or plant part thereof, one or more copies of a transgene comprising at least one nucleotide sequence of a tdcB gene encoding catabolic threonine dehydratase (E.C.4.2.1.19), thereby enhancing resistance to a herbicide.

* * * * *

SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<221> NAME/KEY: misc_feature
<223> OTHER INFORMATION: Primer

<400> SEQUENCE: 1
gggaattcgg tgtcggttac ggttacct              28

```
<210> SEQ ID NO 2
<211> LENGTH: 28
<212> TYPE: DNA
<213> ORGANISM: Artificial Sequence
<220> FEATURE:
<221> NAME/KEY: misc_feature
<223> OTHER INFORMATION: Primer

<400> SEQUENCE: 2
ccggtacccc aaacaagcct aacgtcca                                           28

<210> SEQ ID NO 3
<211> LENGTH: 30
<212> TYPE: DNA
<213> ORGANISM: Artificial Sequence
<220> FEATURE:
<221> NAME/KEY: misc_feature
<223> OTHER INFORMATION: Primer

<400> SEQUENCE: 3
ggaattcatg agtgaaacat acgtgtctga                                         30

<210> SEQ ID NO 4
<211> LENGTH: 24
<212> TYPE: DNA
<213> ORGANISM: Artificial Sequence
<220> FEATURE:
<221> NAME/KEY: misc_feature
<223> OTHER INFORMATION: Primer

<400> SEQUENCE: 4
ccacgcgtgg ggctttgcga tcct                                               24
```